(12) United States Patent
Mancl et al.

(10) Patent No.: US 12,027,265 B2
(45) Date of Patent: Jul. 2, 2024

(54) METHOD AND SYSTEMS FOR INTEGRATED ALERT MANAGEMENT

(71) Applicant: GE Precision Healthcare LLC, Wauwatosa, WI (US)

(72) Inventors: Ryan Mancl, Grapevine, TX (US); Tamas Fixler, Thornhill (CA)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 17/808,395

(22) Filed: Jun. 23, 2022

(65) Prior Publication Data
US 2023/0005615 A1    Jan. 5, 2023

Related U.S. Application Data

(60) Provisional application No. 63/216,800, filed on Jun. 30, 2021.

(51) Int. Cl.
| | | |
|---|---|---|
| *G06F 3/0482* | (2013.01) | |
| *G06F 3/04847* | (2022.01) | |
| *G16H 10/60* | (2018.01) | |
| *G16H 40/67* | (2018.01) | |

(52) U.S. Cl.
CPC ............ *G16H 40/67* (2018.01); *G06F 3/0482* (2013.01); *G06F 3/04847* (2013.01); *G16H 10/60* (2018.01)

(58) Field of Classification Search
CPC ........ G16H 40/67; G16H 10/60; G16H 40/20; G06F 3/0482; G06F 3/04847
See application file for complete search history.

(56) References Cited

U.S. PATENT DOCUMENTS

| | | | | |
|---|---|---|---|---|
| 9,164,656 | B1* | 10/2015 | Keller | G05B 19/41865 |
| 9,240,002 | B2* | 1/2016 | Hume | G06Q 10/10 |
| 10,964,427 | B2 | 3/2021 | Day et al. | |
| 2009/0326340 | A1* | 12/2009 | Wang | A61B 5/002 |
| | | | | 600/301 |
| 2011/0080294 | A1* | 4/2011 | Tanishima | A61B 5/1455 |
| | | | | 600/301 |
| 2011/0106558 | A1* | 5/2011 | Solito | G16H 10/60 |
| | | | | 706/54 |
| 2011/0106561 | A1* | 5/2011 | Eaton, Jr. | G16H 80/00 |
| | | | | 705/2 |

(Continued)

OTHER PUBLICATIONS

CA application 3,165,997 filed Jun. 28, 2022—Examiner's Report issued Sep. 20, 2023; 5 pages.

*Primary Examiner* — Dino Kujundzic
(74) *Attorney, Agent, or Firm* — McCoy Russell LLP

(57) ABSTRACT

Various methods and systems are provided for integrated alert management for clinical decision support. In one embodiment, a method includes determining an alert for a patient relating to a task for caring for the patient, displaying, to a user, the alert via a graphical user interface, responsive to receiving a selection by the user via the graphical user interface, performing one or more actions including adjusting a status of the alert, snoozing the alert for a specified duration, escalating the alert to one or more users, adding a comment on the alert, and displaying a history of interactions with the alert. In this way, hospital staff may easily manage alerts and tasks associated with a patient in an integrated graphical user interface.

16 Claims, 16 Drawing Sheets

(56) References Cited

U.S. PATENT DOCUMENTS

| | | | |
|---|---|---|---|
| 2012/0169467 A1* | 7/2012 | Condra | G16H 40/20 |
| | | | 340/8.1 |
| 2014/0184408 A1* | 7/2014 | Herbst | G16H 10/60 |
| | | | 340/539.12 |
| 2017/0102846 A1* | 4/2017 | Ebler | G06F 3/04847 |
| 2017/0109018 A1* | 4/2017 | Vaglio | H04W 4/16 |
| 2019/0108908 A1* | 4/2019 | Faulks | G08B 27/005 |
| 2020/0327996 A1* | 10/2020 | Barkol | G16H 80/00 |
| 2021/0057111 A1* | 2/2021 | Barkol | H04L 51/046 |
| 2021/0059616 A1* | 3/2021 | Abrol | A61B 5/7435 |
| 2021/0065888 A1* | 3/2021 | Page | G06F 3/14 |
| 2021/0085868 A1 | 3/2021 | Lim | |
| 2021/0098090 A1 | 4/2021 | Thomas et al. | |
| 2021/0298690 A1* | 9/2021 | Varga | A61B 5/746 |
| 2022/0027856 A1* | 1/2022 | Piaskowski | G06Q 10/105 |
| 2022/0184309 A1* | 6/2022 | Rosinko | G08B 21/02 |

* cited by examiner

Single alerts

| Time since Alert | Patient | Unit & Bed |
|---|---|---|
| 3h 50m | A.JAR 0751282828 | 9K12AS |
| 1h 48m | R.POR 0927361521 | 10A201 |

FIG. 11

Multiple alerts

| Time since Initial Concern | Patient | Delayed Actions | Unit & Bed |
|---|---|---|---|
| 12h 45m | L.WAS 8371927162 | | 8S14 |
| 10h 12m | T.GAR 0456172812 | | 11K10 |
| 10h 6m | E.WER 0728192718 | | 9S2114 |
| 9h 54m | G.VER 0751282821 | | 10A201 |
| 9h 23m | T.GUR 0291827163 | | 10C101 |
| 6h 21m | T.DIN 0291827162 | | 9C205 |
| 5h 15m | S.DEN 0291998162 | | D35 |

| | GI patient not ready<br>Check-In 07/09/2020 05:00 | PRU,R<br>100828144 | F00201 | |
|---|---|---|---|---|
| | GI patient not ready<br>Check-In 07/09/2020 05:00 | PRU,R<br>100828144 | F00201 | |
| | GI patient not ready<br>Check-In 07/09/2020 05:00 | PRU,R<br>100828144 | F00201 | |

| Alert management | |
|---|---|
| Patient | |
| G.GLO  0123456789 | |
| Alert | Status |
| MRI delay | |
| Abnormal lab value | |

| Alert management | |
|---|---|
| Patient | |
| G.GLO  0123456789 | |
| Alert | Status |
| MRI delay | |
| Abnormal lab value | |

FIG. 14

T.FIX 90092031　✓　♿　🔔 (Indefinite)　3E-3333-01

| Ordering MD | Order number |
|---|---|
| John Doe | 13510979697 |

| Exam type | Elapsed time |
|---|---|
| MRI spine Cervical w/ + w/o contrast | 2d 3h |

Multi modality

2 Alerts

🧪　Abnormal creatinine　　✓　🔔　💬　✎

♿　Tele transport　　✓　🔔　💬　✎

2 Attributes (Acuity)　Carotid dissection

→　Discharge order

Comments

The patient is ready

Escalation comment

Escalate this alert

Snooze comment

Escalate this alert

Assigned to:

John Doe

PM - Downgrade expediter

[CC] [R] [<<] [Profile default >] 🗔 🗄 🔍 ⓘ ⚙

| Patient | LOC. | DG. RD./acuity | | | Criteria | Alerts | | |
|---|---|---|---|---|---|---|---|---|
| G.DAW 90123456 | CES 5312-CI | ☐ | CRL CCS 15 | PASS 0 | | Get Adv Dir ● ○ | Post DC FU appt ○ | Arrange transport ○ |
| W.DIS 91234567 | NT2 2458-H1 | Ready for DG CCS 15 | | PASS 0 | Lumbar drain ○ | Document DCP ● ○ | Pending CT ○ | PT Eval △ |
| D.DUC 92345678 | NT3 3157-H1 | Possible DG CCS 14 | | PASS 0 | Vasoactive mode(1) ○ | Med Rec △ ○ | | |
| W.POO 93456789 | W2L 2245-W1 | Not eligible CCS 1 | | PASS -1 | Ventilator △ ○ | | | |
| M.MOU 94567891 | E2TP 2106-EI | Not eligible CCS 1 | | PASS -4 | Vasoactive mode(1) | Abnormal HR ○ | Valved PCC ○ | Pending XR ○ | Med Rec ○ |

METHOD AND SYSTEMS FOR INTEGRATED ALERT MANAGEMENT

CROSS-REFERENCE TO RELATED APPLICATIONS

The present application claims priority to U.S. Provisional Patent Application No. 63/216,800, entitled "METHOD AND SYSTEMS FOR INTEGRATED ALERT MANAGEMENT," and filed Jun. 30, 2021, the entire contents of which is hereby incorporated by reference for all purposes.

FIELD

Embodiments of the subject matter disclosed herein relate to patient care protocol management, and more particularly, to integrated alert management for patient care.

BACKGROUND

Patient care can be organized according to one or more care pathways including milestones, tasks, resources, and personnel to care for the patient. Certain care pathways are known, along with associated clinical metrics which indicate a patient's health state. Such clinical metrics can be monitored by care providers to help ensure they are stable. When stable, the care providers are able to handle a clinical workflow and a hospital's physical resources have capacity. Ongoing and evolving care delivery protocols vary in response to changes in managed clinical measures over time, and their clinical effects are influenced by the accumulated interactions of a patient with the hospital's physical environment as well as dissociated routine actions of a plurality of care providers, staff, and visitors.

BRIEF DESCRIPTION

In one embodiment, a method comprises determining an alert for a patient relating to a task for caring for the patient, displaying, to a user, the alert via a graphical user interface, responsive to receiving a selection by the user via the graphical user interface, performing one or more actions including adjusting a status of the alert, snoozing the alert for a specified duration, escalating the alert to one or more users, adding a comment on the alert, and displaying a history of interactions with the alert. In this way, hospital staff may easily manage alerts and tasks associated with a patient in an integrated graphical user interface.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 3 shows an example user interface of a command center engine, according to an embodiment;

FIG. 6 shows a diagram the GUI of FIG. 4 with a sub-menu for managing an alert snooze in an expanded state, according to an embodiment;

FIG. 7 shows a diagram illustrating the GUI of FIG. 4 with a sub-menu for managing an alert comment in an expanded state, according to an embodiment;

FIG. 8 shows a diagram illustrating the GUI of FIG. 4 with a sub-menu for managing an alert escalation in an expanded state, according to an embodiment;

FIG. 9 shows a diagram illustrating a display panel for managing an alert history in an expanded state, according to an embodiment;

FIG. 10 shows a diagram illustrating the GUI of FIG. 4 with a sub-menu for managing an alert deletion in an expanded state, according to an embodiment;

FIG. 11 shows a diagram illustrating an example graphical user interface for managing an alert status for single alerts per patient, according to an embodiment;

FIG. 12 shows a diagram illustrating an example graphical user interface for managing an alert status for multiple alerts per patient, according to an embodiment;

FIG. 13 shows a diagram illustrating example graphical user interfaces for conveying an integrated alert status, according to an embodiment;

FIG. 14 shows a diagram illustrating the GUI of FIG. 4 highlighting icons for managing alert priority, according to an embodiment;

FIG. 15 shows a diagram illustrating an example graphical user interface for depicting alert information upon hovering, according to an embodiment;

FIG. 16 shows a diagram illustrating another example graphical user interface for an integrated alert manager, according to an embodiment;

FIG. 17 shows the GUI of FIG. 16 with a sub-menu in an expanded state, according to an embodiment;

FIG. 19 shows a diagram illustrating an example graphical user interface for a patient downgrade status module, according to an embodiment;

DETAILED DESCRIPTION

The following description relates to various embodiments of integrated alert management. In particular, systems and methods for integrated alert management are provided. Hospitals and other clinical facilities may provide computing systems with graphical user interfaces (GUIs) for displaying patient information to healthcare providers and other users. In this way, a healthcare provider may view the most up-to-date patient information and retrieve data from electronic health records, imaging results, laboratory results, and so on. Further, alerts may be automatically and/or manually generated to indicate tasks associated with a patient. Such alerts may become unwieldy or less useful in an environment such as an intensive care unit (ICU). For example, patients being treated in an ICU may each be associated with multiple different alerts of different priority and assigned to different healthcare providers, and various alerts may be triggered by different computing systems and presented to healthcare providers via different GUIs. Some GUIs may allow certain actions to be taken regarding an alert (e.g., snoozing an alert or escalating an alert) while other GUIs may allow other, different actions to be taken regarding an alert (e.g., commenting on an alert, deleting an alert). When the alerts are managed across different GUIs, actions taken on an alert via on GUI may not be propagated to the other GUIs, meaning that all relevant healthcare providers may not be informed when an action on an alert has been performed. Further, some actions may be mutually exclusive or conflict with one another (e.g., escalating an alert that has been marked complete) and managing an alert across multiple different GUIs may allow conflicting actions to occur. These issues may lead to missed alerts, redundant alerts, or other situations that may waste healthcare provider time or compromise patient care. Further, managing an alert across multiple different GUIs may lead to inefficient usage of computing resources, such as redundant information storage, increased network traffic, and inefficient usage of processing resources when conflicting actions are allowed to occur.

The methods and systems provided herein provide integrated alert management in a single graphical user interface that enables users to easily review alerts, adjust the status of the alerts, snooze or dismiss the alerts, escalate the alerts, prioritize the alerts, and so on. These interactions with the alerts may be applied to the display of such alerts to other users. In this way, alerts may be effectively managed so that healthcare providers may be able to prioritize care to patients in a timely manner without being overwhelmed by information in a high-stress environment.

Figure 1:
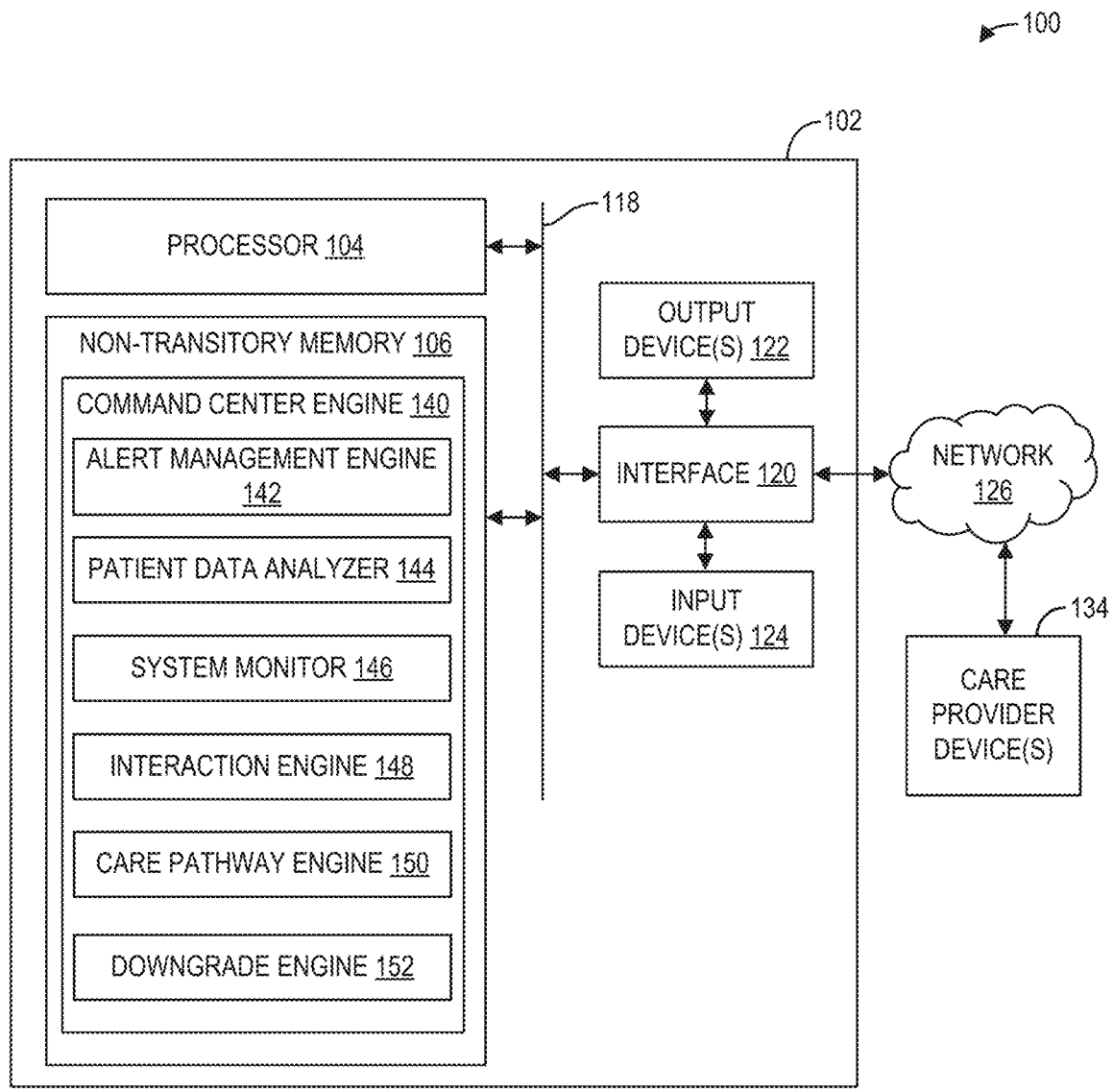
FIG. 1 shows a block diagram of an example computing system for integrated alert management, according to an embodiment.

Referring now to FIG. 1, a computing system 100 is shown, in accordance with an exemplary embodiment. Computing system 100 comprises a computing device 102 which may comprise, as illustrative and non-limiting examples, a server, a personal computer, a workstation, a mobile device (e.g., a cellular phone, a smart phone, a computing tablet, and so on), or any other type of computing device.

The computing device 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual hardware components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

The computing device 102 further includes non-transitory memory 106. It should be appreciated that the computing device 102 may include additional memory devices, including volatile memory, mass storage, local memory, and so on. The non-transitory memory 106 a command center engine 140.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration. The processor 104 and the non-transitory memory 106 may be coupled, for example, via a communications bus 118.

The computing device 102 may further include an interface 120 communicatively coupled to the processor 104 and the non-transitory memory 106 via the communications bus 118. The interface 120 may be implemented by one or more of any type of interface standard, such as an Ethernet interface, a universal serial bus (USB), a BLUETOOTH interface, a near field communication (NFC) interface, and/or a PCI express interface.

The computing device 102 may further include one or more output device(s) 122 communicatively coupled to the processor 104 and the non-transitory memory 106 via the interface 120. The output device(s) 122 may comprise, for example, one or more display devices. Such a display device may include one or more display devices utilizing virtually any type of technology (e.g., a light emitting diode (LED), an organic light emitting diode (OLED), a liquid crystal display (LCD), a cathode ray tube (CRT) display, an in-place switching (IPS) display, a touchscreen, and so on). In some embodiments, output device 122 may comprise a computer monitor configured to display medical information of various types and styles. Output device(s) 122 may be combined with processor 104, non-transitory memory 106, and/or user input device(s) 124 in a shared enclosure, or may be a peripheral display device and may comprise a monitor, touchscreen, projector, or other output device known in the art, which may enable a user to view decision support output (e.g., alerts) according to one or more embodiments of the current disclosure, and/or interact with various data stored in non-transitory memory 106.

The computing device 102 may further include one or more user input device(s) 124 coupled to the processor 104 and the non-transitory memory 106 via the interface 120. A user input device 124 may comprise, for example, one or more of a touchscreen, a keyboard, a mouse, a trackpad, a motion sensing camera, a microphone, or other device configured to enable a user to interact with and manipulate data within computing device 102.

The interface 120 may further include a communication device such as a transmitter, a receiver, a transceiver, a modem, a residential gateway, a wireless access point, and/or a network interface to facilitate exchange of data with external machines (e.g., computing devices of any kind) via a network 126. The communication may be via, for example, an Ethernet connection, a digital subscriber line (DSL) connection, a telephone line connection, a coaxial cable system, a satellite system, a line-of-site wireless system, a cellular telephone system, and so on. As a non-limiting example, FIG. 1 shows one or more care provider devices 134 that may be communicatively coupled to computing device 102. Each care provider device may include a processor, memory, communication module, user input device, display (e.g., screen or monitor), and/or other subsystems (similar to the processor, memory, communication module, user input device, and output device of computing device 102) and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. As will be explained in more detail below, the care provider devices may display graphical user interfaces described herein (including alerts generated by an alert management engine 142) and may facilitate user interaction with the graphical user interfaces (e.g., to snooze, dismiss, or perform other actions for an alert).

The command center engine 140 may comprise a care pathway management system configured to enable evolving state protocols and decision support associated with patient care pathways. The command center engine 140 includes, as an illustrative and non-limiting example, an alert management engine 142, a patient data analyzer 144, a system monitor 146, an interaction engine 148, and a care pathway engine 150. The patient data analyzer 144 processes available patient data for patients of a healthcare facility to understand the patient population and associate them with application care pathway(s) to which patients are assigned, should be assigned, and so on. The care pathway engine 150 models tasks for protocols and other actions associated with each available care pathway and correlates with the patient data analyzer 144 to determine patient status along a care pathway, update a care pathway based on changes to tasks associated with the care pathway, and so on. The system monitor 146 monitors a total resource load on the healthcare facility from patients and pathways and draws information from the patient data analyzer 144 and the care pathway engine 150 to monitor patient progress along a care pathway, evaluate which patients should be on which pathways, predict likely outcomes for patients on and off particular pathways, and so on.

The interaction engine 148 enables one or more users and/or external systems (e.g., an electronic medical record system, a picture archiving and communication system, a radiology desktop, an imaging workstation, an administrative workstation, and so on) to interact with patient and/or care pathway information via the system monitor 146, care pathway engine 150, patient data analyzer 144, alert management engine 142, and downgrade engine 152. For example, changes can be made to patient records, care pathway prescriptions, associated protocols/tasks, and so on, via the interaction engine 148. A display driver may generate a graphical user interface to display information on an output device 122 such as a display screen, for example, and facilitate interaction with the interaction engine 148.

The alert management engine 142 integrates into any graphical user interface or graphical user interface module (e.g., a tile) for enabling alert management. As described further herein with regard to FIG. 2, the alert management engine 142 provides alerts or tasks relating to a patient responsive to electronic medical record (EMR) signals and/or manual input, and further enables management of the alert by selectively allowing a user to change a status of the alert, snooze or dismiss the alert, escalate the alert, comment on the alert, view history of the alert and actions relating to the alert, delete the alert, and so on.

The downgrade engine 152 looks at a series of alerts from the alert management engine 142, for example, for a patient and determines whether the patient is ready to be downgraded from a current health status. For example, if a patient is in an intensive care unit (ICU), the downgrade engine 152 evaluates alerts relating to the patient to identify when the patient is ready to be downgraded from the ICU. As an illustrative example, the downgrade engine 152 looks at alerts regarding whether the patient is currently on a ventilator, currently on a medication drip that may only be administered in ICU, and so on. The downgrade engine 152 includes a configuration table that lays out all possible combinations of such alerts and maps each combination to a specific clinical state of the patient that pertains to the readiness of the patient to downgrade from a current level of care to a lower level of care. As an illustrative example, the downgrade engine 152 may evaluate a combination of criteria (e.g., alerts or other tasks relating to a patient), and determines that the patient is not eligible for a lower level of care, that the patient is possibly ready for downgrade where a human's clinical judgment is needed, or that the patient is ready for downgrade (i.e., there is an absence of any clinical criteria or combination of criteria that would prevent the patient from being released from ICU). The downgrade engine 152 determines the patient state from rule-based inputs from the EMR.

It should be understood that computing system 100 shown in FIG. 1 is illustrative and non-limiting, and that another appropriate computing system 100 may include more, fewer, or different components.

Figure 2:
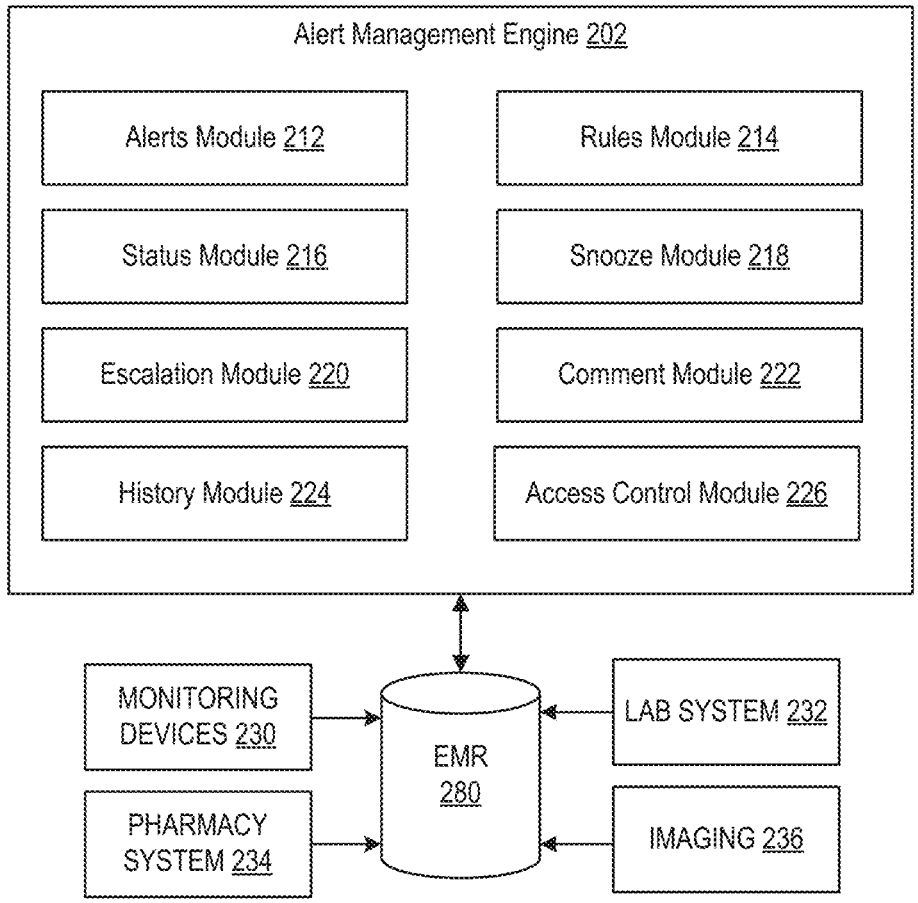
FIG. 2 shows a block diagram of an example module architecture for integrated alert management, according to an embodiment.

FIG. 2 shows a block diagram of an example alert management system 200 for integrated alert management, according to an embodiment. The alert management system 200 includes an alert management engine 202 which may comprise the alert management engine 142 of the command center engine 140, as an illustrative and non-limiting example. The alert management engine 202 may include an alerts module 212, a rules module 214, a status module 216, a snooze module 218, an escalation module 220, a comment module 222, a history module 224, and an access control module 226.

The alerts module 212 generates alerts for patients responsive to automatic triggers (e.g., from EMR signals) and/or manual commands. The rules module 214 stores rules for evaluating EMR signals, for example, to determine alerts based on the EMR signals, determine if alerts are resolved based on EMR signals, and/or manage conflicts between requested alert actions. The status module 216 manages a status of an alert (e.g., complete, in progress, or incomplete). The status module 216 may further manage a priority of the alert. The snooze module 218 enables a user to snooze or temporarily dismiss an alert for a set amount of time. The escalation module 220 enables a user to escalate an alert to one or more users or departments. The comment module 222 enables a user to provide a comment on an alert.

The alert management engine operates globally across all users of the command center engine/alert management engine. For example, if one user snoozes an alert, then all users will see that alert as snoozed. This applies for all actions taken in Alert Manager. In some examples, the Alert Manager may have an edit feature provided via access control module 226 that enables permissions/actions for each alert to be controlled at the user, group, or core level. For example, permissions for any action may be managed at the user group level so that a local team can adjust a specific alert or alert type to meet their specific implementation. Any of the tabs may be optional at the core level, so that all uses of alert manager will not leverage all possible functions. In this case the user should not be able to configure access to that feature. In the manage tab there are four individual components that may be configurable for each alert. In the snooze/dismiss tab, the ability to snooze, dismiss, or both should be possible; this is configurable at a core tile level. All configurations described are at the "pencil" level. If there are multiple areas or views in a tile that use the manage function differently, they should have their own set of configurations.

Alerts may be filtered or sorted at the user level so that a user may quickly find and view only desired alerts. For example, a user may apply a filter to view only escalated alerts, or view only currently-active alerts. All filters should apply regardless of alert manager values. This will ensure that if snoozed or dismissed alerts are hidden/exposed that there is no conflict with order of operations. All sorts should apply regardless of alert manager values. This will ensure that if snoozed or dismissed alerts are hidden/exposed that there is no conflict with order of operations. All configurator options should apply regardless of alert manager values. This includes trigger criteria. If an alert no longer meets the trigger criteria it will disappear from the tile. If it then meets the criteria again, the alert should reappear in a snoozed state.

The access control module 226 controls access to different functions of the alert management engine 202. Access to alert manager functions may be defined at a tile by tile level. The level of access may be at the following levels: User Can Snooze (Y/N), User Can Dismiss (Y/N), User Can Reactivate (Y/N), User Can Manage (Y/N), User Can Mark In Progress (Y/N), User Can Assign (Anyone, Self Only, No), User Can Configure Tile (Y/N), User Can Mark Priority (Y/N).

The history module 224 logs any and all action taken by a user regarding an alert. This history may be maintained such that it can be displayed on the tile and audited against. The information includes user ID, time of event, action taken, and any reason comments associated.

As explained above, the alerts module 212 generates alerts for patients responsive to automatic triggers, which may include triggers from EMR signals. As such, the alert management engine 202 is communicatively coupled to an EMR database 280. EMR database 280 may store electronic medical records (EMRs) for a plurality of patients. An EMR for a patient may include patient demographic information, family medical history, past medical history, lifestyle information, preexisting medical conditions, current medications, allergies, surgical history, past medical screenings and procedures, past hospitalizations and visits, etc. EMR database 280 be an external database accessible via a secured hospital interface, or EMR database 280 may be a local database (e.g., housed on a device of the hospital). EMR database 280 may be a database stored in a mass storage device configured to communicate with secure channels (e.g., HTTPS and TLS), and store data in encrypted form. Further, the EMR database is configured to control access to patient electronic medical records such that only authorized healthcare providers may edit and access the electronic medical records.

Further, alert management engine 202 may communicate with other data sources that may supply triggers for generating alerts, such as lab system 232, pharmacy system 234, one or more monitoring devices 230, and imaging services 236. Other systems may be communicatively coupled to the alert management engine 202 (directly and/or through EMR database), such as a computerized provider order entry (CPOE) system (which may track/manage provider orders such as treatments, tests, hospital ward/unit assignment changes, and the like) and the like.

The lab system 232 may include one or more computing devices associated with an on-site or off-site laboratory that performs lab tests on patient specimens. The one or more computing devices may include resources (e.g., memory and processors) allocated to store and execute a laboratory information system (LIS). The LIS may manage various aspects of the laboratory procedures, such as managing/assisting with tagging of incoming specimens (e.g., with patient and care provider information, test(s) to be conducted on the specimen, and so forth), tracking specimens (e.g., in storage, being processed), generating reports of test results, and the like. Accordingly, the LIS may interface directly with various laboratory equipment, such as mass spectrometers, chromatographers, analyzers, etc., and thus may have knowledge of which specimens are currently being tested, the results of such tests, and the performance status of the various pieces of equipment. The lab system 232 may send lab results to EMR database 280, and the lab results may be included in the EMR signals. Additionally or alternatively, the lab system 232 may send lab results directly to alert management engine 202, at least in some examples, and thus the alert management engine 202 may receive lab signals from which alerts may be generated.

The pharmacy system 234 may include one or more computing devices associated with an on-site or off-site pharmacy that fills prescriptions as ordered by care provider (s). The one or more computing devices of the pharmacy system may include resources (e.g., memory and processors) allocated to receive prescription requests and communicate the requests with pharmacy staff, track prescription fill status, notify an ordering care provider when a prescription is available, and so forth. The pharmacy system 234 may send prescription notifications to EMR database 280, and the prescription notifications may be included in the EMR signals. Additionally or alternatively, the pharmacy system 234 may send notifications regarding prescriptions directly to alert management engine 202, at least in some examples, and thus the alert management engine 202 may receive pharmacy signals from which alerts may be generated.

The monitoring devices 230 may include traditional medical devices monitoring respective patients, such as pulse oximeters, heart rate monitors, blood glucose monitors, and ECGs, as well as microphones, cameras, and other devices. The monitoring devices 230 may send output directly to the alert management engine 202 and/or may send output to the EMR database 280. The imaging services 236 may include a radiology information system (RIS), a picture archive and communication system (PACS), and/or other computing devices associated with diagnostic imaging. The computing devices comprising the imaging services 236 may manage scheduling of diagnostic imaging exams, recommend and execute scanning protocols to perform diagnostic imaging exams, process imaging data to generate images, save diagnostic images in memory, etc. The imaging services 236 may send information/signals regarding diagnostic imaging to the EMR database 280 and/or directly to the alert management engine 202.

Figure 3:
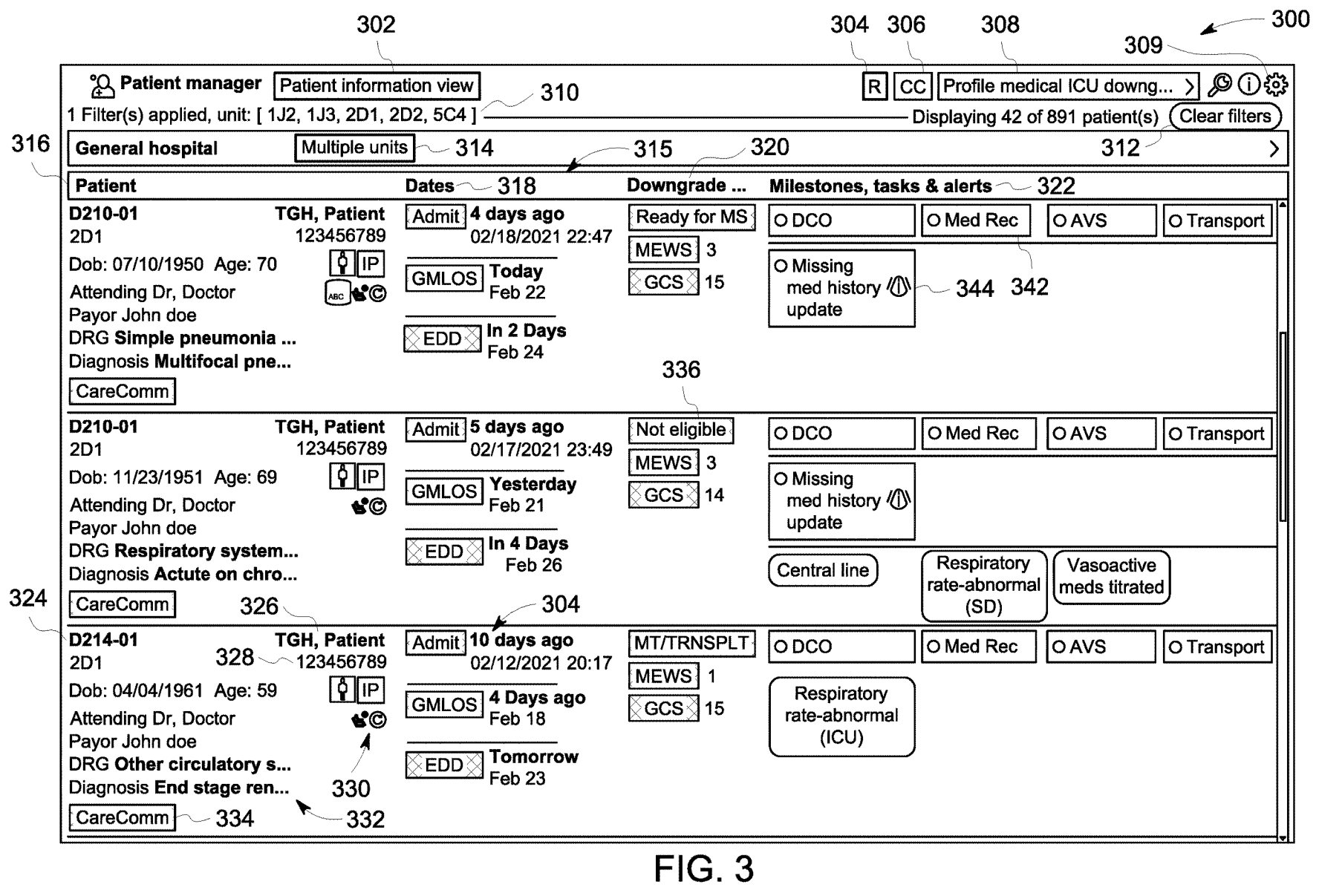

Turning to FIG. 3, a first embodiment of a graphical UI 300 is shown of a command center engine, such as the command center engine of FIG. 1. UI 300 may be displayed on a display device (e.g., a display device of a care provider device 134). Specifically, UI 300 may be displayed to a care provider when the care provider uses the command center engine to view patient information for one or more patients within a selected ward, unit, or other aspect of a medical facility.

Figure 16:
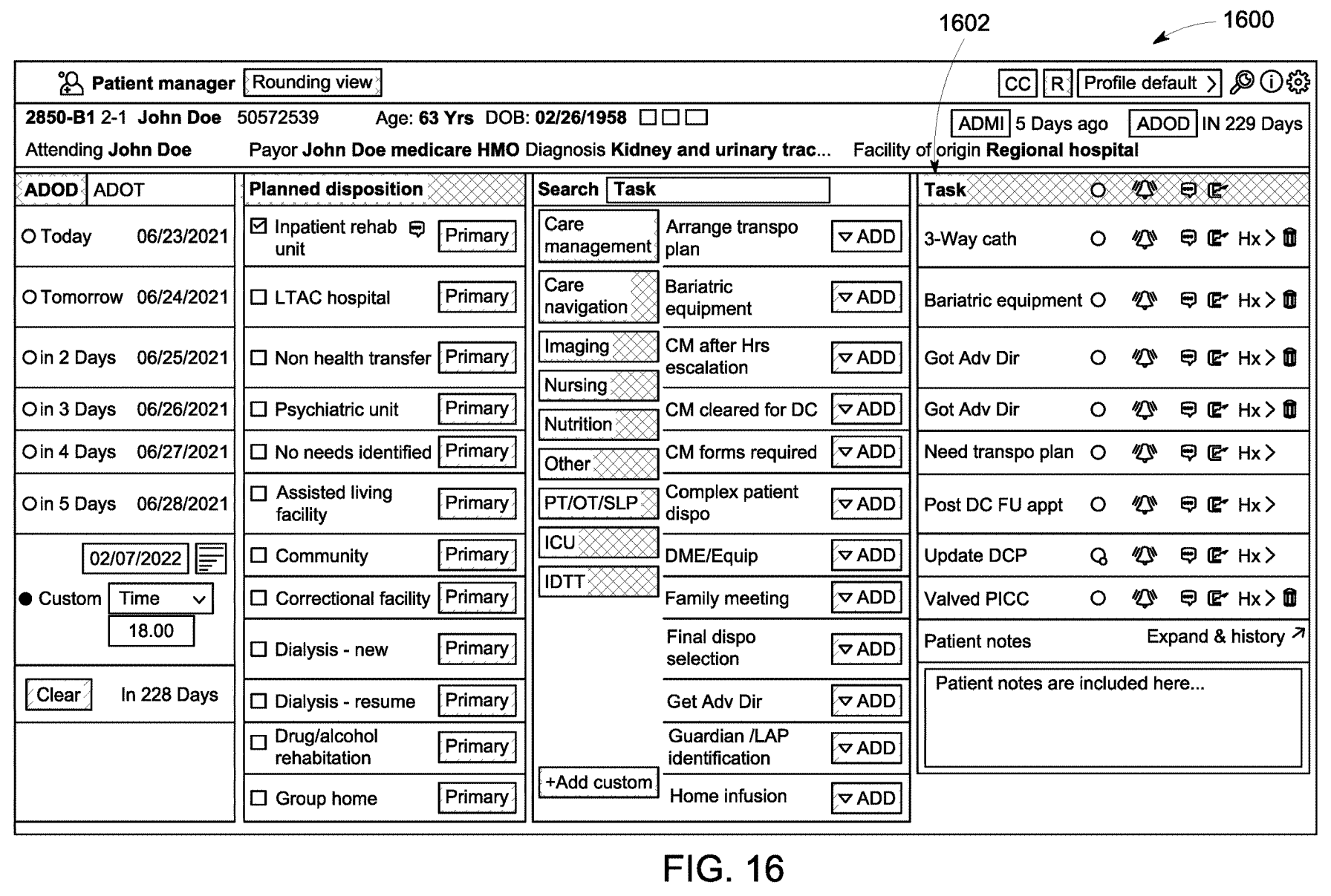

As shown, UI 300 is in a patient information view, as indicated by view field 302. The UI 300 may be displayed in different alternative views. In some embodiments, the UI 300 may be displayed either in an enhanced or rounding view (an example of which is shown in FIG. 16), where information is displayed in a fixed format that is not customizable by the user, or in a condensed or command center view, where less information is displayed in a variable format that is customizable by the user. The user may customize the condensed view by hiding one or more columns, rows, sections, or elements of the enhanced view. For example, a first user may view the UI 300 in a first condensed view that is customized to hide a first portion of patient data displayed in the UI 300, in order to view more rows (e.g., patients) in a single screen. A second user may view the UI 300 in a second condensed view that is customized to hide a column of the UI 300, in order to better view data displayed in a different column. A third user may view the UI 300 in a third, enhanced view, in order to view a comprehensive set of data. Each of the first user, the second user, and the third user may select a desired view and/or switch between desired views by selecting one or more controls of the UI 300, such as a rounding view toggle switch 304 or a command center view toggle switch 306.

The UI 300 may include a hospital unit selection element 314, which may dictate which patients' information is displayed on UI 300. In some embodiments, the hospital unit selection element 314 may comprise a drop-down list of hospital units, where each suitable hospital unit may be included as an item of the drop-down list that may be selected by a user. Suitable hospital units may include various types of ICUs, including pediatric ICUs, neo-natal ICUs, and/or ICUs for different types of medical conditions (neuroscience ICU, cancer ICU, etc.). Suitable hospital units may also include other types of specialty hospital units where a greater or more specific level of care is provided than may be provided at a typical floor care unit of a hospital and/or may include typical floor care units of a hospital. Using hospital unit selection element 314, the user may select a desired hospital unit or choose to see an aggregate view of all hospital units in a hospital, hospital network, or healthcare organization.

In some embodiments, when a hospital unit (e.g., an ICU) is selected, a display panel 315 may be automatically updated to generate and show downgrade recommendations for patients of the selected hospital unit. In other embodiments, the display panel 315 may not be automatically updated, and the user may initiate display of downgrade recommendations by selecting a different control element (not shown in FIG. 3), such as a "display downgrade recommendations" button.

When a hospital or suitable hospital unit is selected via the hospital unit selection element 314, a name or identifier of the hospital or suitable hospital unit may be displayed in a profile element 308 of the UI 300. Via the profile element 308, the user may select a desired profile for how the information displayed via UI 300. For example, the selected profile may highlight or emphasize downgrade readiness/ recommendations, and thus include the display panel 315. Other profiles may highlight or emphasize other factors, such as alerts/tasks, which will be explained in more detail below. Additionally, in some embodiments, one or more filters may be applied to the UI 300 to filter patient data shown in the UI 300. The one or more filters may be selected, for example, via controls accessible via a settings button 309. A summary of one or more filters applied may be displayed in the filter bar 310, and a user may clear the one or more filters via a clear filters button 312 included in the filter bar 310.

As one example, a user may have time allotted to schedule patients for diagnostic imaging, and thus may want to view all patients who have diagnostic imaging exams ordered but not scheduled. The user may select to filter patients by an "imaging delay" alert, which may result in UI 300 displaying only patients who need a diagnostic imaging exam scheduled and performed. As another example, a user may desire to view all patients with escalated alerts, and thus the user may select a filter to show only patients with escalated alerts.

In the embodiment shown in FIG. 3, downgrade recommendations and patient tasks/alerts may be displayed in rows of UI 300, where each row corresponds to a patient of the selected hospital unit. The downgrade recommendations and other information may be displayed in columns of UI 300. In other embodiments, a layout of the information may be different. For example, in other embodiments, each patient of the selected hospital unit may be displayed in a separate column, and the downgrade recommendations and other information may be displayed in rows of UI 300. It should be appreciated that the layout and juxtaposition of the elements of UI 300 may vary in different embodiments, and the elements may appear in different visual configurations without departing from the scope of this disclosure. Additionally, not all of the elements shown in UI 300 may be included in an embodiment, and some embodiments may include a greater or lesser number of elements.

UI 300 may include a patient info column 316, which may show identifying and general information of a patient. For each row of UI 300, a patient data panel 332 that includes patient information may be displayed for a corresponding patient in the patient info column 316. The patient data panel 332 may include a patient name (or abbreviated name) 326 and/or an identification number 328. A location code 324 may be included in the patient data panel 332, which may indicate a current location of the patient in the hospital or hospital system (e.g., the unit to which the patient has been assigned and/or is currently registered). The patient data panel 332 may also include other general information, such as, for example, an age and/or date of birth of the patient, an attending physician of the patient, patient insurance information, a diagnosis of the patient, and the like. Further, in the example shown, some aspects of patient information (such as whether a patient is a new admission or a readmission) may be visualized via icons, such as icon 330.

In some embodiments, a care communication button 334 may be included in the patient data panel 332, which when selected may generate an alert that may be sent to other care providers and/or saved as part of the patient's EHR to indicate that an ordered or commanded patient task has yet to be initiated or completed. However, in some examples, the care communication button 334 may be omitted or may trigger other types of communication or alerts.

UI 300 may include a dates column 318, which may show a timeline of events relating to changes in a status of the patient during a time spent by the patient in the hospital, including dates and times of the events. In some embodiments, the timeline may begin at a time of admission of a patient, and may include dates and times of expected discharge, such as a projected discharge date (e.g., an expected discharge data, EDD) and/or a mean length of stay for patients with the same condition as the patient (e.g., a geometric mean length of stay, GMLOS).

UI 300 may include a downgrade readiness column 320, which may include a downgrade recommendation 336 for a patient (e.g., visually indicating a recommendation on whether the patient may be downgraded in preparation for a transfer to a different care unit or not). In some embodiments, a set of possible downgrade recommendations may be pre-defined, where downgrade recommendation 336 may be a most appropriate downgrade recommendation element based on the set of possible downgrade recommendations. The patient downgrade recommendation system may assign the most appropriate downgrade recommendation based on applying a set of rules corresponding to different patient data according to various downgrade criteria.

For example, in some embodiments, the set of possible downgrade recommendations 336 may include a "Ready for MS" recommendation which may indicate that a patient is eligible for a transfer to another unit, herein the medical-surgical floor/unit; a "Ready for SD" recommendation, which may indicate that the patient is eligible to be transferred to an intermediate "step-down" unit; a "Possible Downgrade" recommendation, which may indicate that the patient may be eligible for a transfer, pending one or more criteria being met that may be predicted to be met soon; a "Lateral Transfer" recommendation, which may indicate that a patient may be eligible for a lateral transfer to a different ICU or unit with a similar level of care; and a "Not Eligible" recommendation, which may indicate that the patient is not eligible for a downgrade. In other embodiments, fewer, additional, or other recommendations may be used.

UI 300 may include a milestones, tasks, and alerts column 322, which may show one or more discharge milestones pending completion, patient alerts (which may include tasks), and/or contributing factors to a downgrade recommendation. In some embodiments, one or more alert elements 344 may be included in a row of UI 300 corresponding to a patient. The one or more alert elements 344 may include patient alerts triggered based on EMR signals, as determined by the alert management engine of FIG. 2. For example, the alert management engine may generate a flag for a patient indicating that the patient is overdue for a test or examination, that certain records or paperwork are missing, that a patient is scheduled for a procedure but has lab results that may put the patient at risk during the procedure, or other suitable alert, which may be displayed as an appropriate alert element on UI 300. The one or more alert elements 344 may also include one or more pending discharge milestones 342, representing tasks to be carried out or completed prior to downgrading the patient or releasing a downgraded patient, pending reports or results, operational logistics involved in transferring the patient, and/or other reminders, warnings, or additional information. In some embodiments, the one or more alert elements 344 may be controls that may be selected. When an alert element is selected, additional information regarding the alert element may be displayed via an additional (e.g., pop-up) display panel.

In some embodiments, the UI 300 may be launched/displayed in response to a request by a care provider when the care provider wishes to view patient information for one or more patients. Additionally or alternatively, the UI 300 may be continuously running, and elements of the patient data may be periodically updated automatically by the command center engine. For example, a care provider may view UI 300 to identify which patients of a plurality of patients have an escalated alert at a first time. At the first time, the care provider may see that no patients have an escalated alert. The care provider may cease viewing of the UI to attend to patients, and return later to view the UI, which may still be running, to view the alert status of the plurality of patients at a second time. In between the first time and the second time, elements of patient data may change, for example, due to more recent data being recorded in the EMR. As a result of the more recent data being recorded, at the second time, the care provider may see that a patient has an escalated alert. Thus, the command center engine, through the UI 300, may serve to provide continuously updated data that may aid the care provider and managing patients of the hospital.

Additionally, data retrieved, accessed, or used by the command center engine may become temporarily or periodically unavailable, for example, if a system or network coupled to the command center engine experiences a failure. In the event that data is unavailable at a time when a care provider is viewing alerts via the UI 300, the command center engine may provide an indication of the unavailability of the data in the UI 300. For example, an alert element may be replaced with a different graphical element indicating that a corresponding alert is pending the availability of the data (e.g., restoration of the system/network that failed).

For example, in order to apply a rule to determine whether a measured lab value of a biomarker of the patient is within a suitable range, the command center engine may attempt to retrieve a recent lab test result from the EMR. A most recent test result retrieved from the EMR may not meet a threshold date or time for being sufficiently recent. In response to the most recent test result not being sufficiently recent, the command center engine may not display an alert for the patient, and may display an alternative element indicating that a sufficiently recent lab test result is unavailable. In some embodiments, the most test result may be indicated along with a date and/or time of the most recent test result.

Thus, while patient data relevant to the alert is updated asynchronously in one or more systems and/or databases coupled to the command center engine, a most recent version of the patient data may be consistently updated and displayed in real time in the UI 300. In this way, the command center engine may provide an efficient and user-friendly way to monitor patient data relating to alerts via a single interface, without having to repeatedly access various EMR systems to ensure accuracy of the patient data and/or while the various EMR systems are in an unlaunched state (e.g., not consuming computing and/or network resources of the healthcare system). An additional advantage of using the command center engine is that errors made inappropriately responding (or failing to respond) to a patient due to patient data that is out of date may be reduced. If the care provider wishes to verify an element of patient data displayed in the UI 300, the care provider may launch a relevant EMR system to verify the element from the patient downgrade recommendation system (e.g., by selecting a downgrade recommendation 336, an alert element 344, a discharge milestone 342, or a different control of the UI 300).

Alternatively, in various embodiments, the care provider may open the command center engine (e.g., to view the UI 300) by first logging into a patient management system of a healthcare network, and selecting a command center/patient manager icon, tile, or similar menu listing of one or more options for retrieving patient data of the patient management system to start the command center and view the UI 300. In still other embodiments, the command center engine may be launched from within a different computer system of a hospital, such as an EMR system, where the command center engine/patient manager may be listed as a selectable menu option within a UI of the EMR system.

Further, via the UI 300, the care provider may view one or more alerts generated for the patient, and initiate any tasks that may be entailed by a transfer order. As the provider completes a task or meets a milestone relevant to the transfer order, the provider may dismiss one or more of the one or more alerts, for example, by selecting a control in a pop-up display panel triggered by selecting an alert, as will be explained in more detail below. The care provider may then confirm the second patient on the list (in order of readiness) in the same manner.

Figure 4:
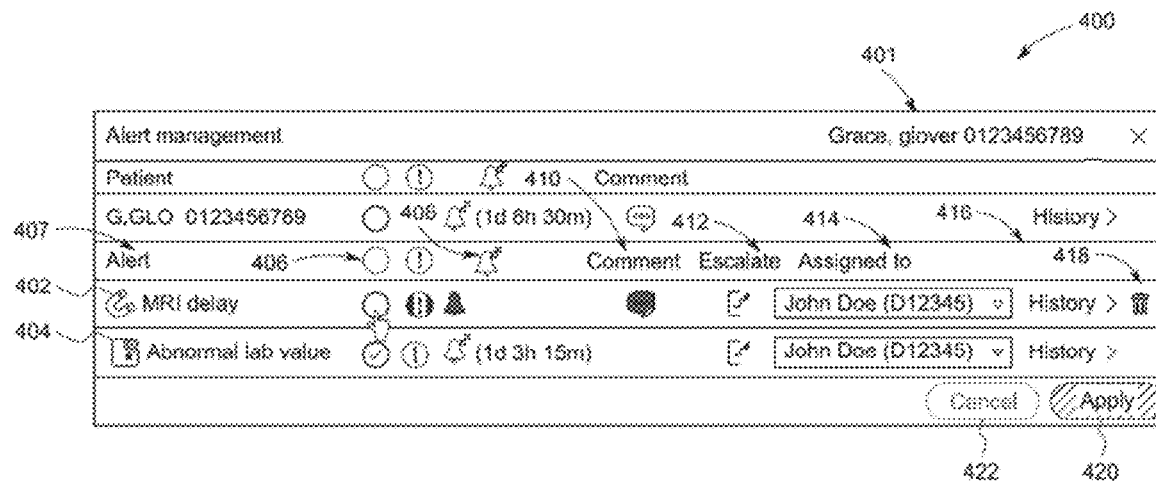
FIG. 4 shows a diagram illustrating an example graphical user interface for an integrated alert manager, according to an embodiment.

FIG. 4 shows a diagram illustrating an example graphical user interface (GUI) 400 for an integrated alert manager, according to an embodiment. GUI 400 may be generated by command center engine 140, using alert management engine 202, in some examples. GUI 400 may be displayed on one or more display devices, such as a display device associated with a care provider device (e.g., one of the care provider devices 134). GUI 400 may present information relating to alerts for one or more selected patients, and thus may also be referred to as an Alert Management GUI. GUI 400 may be displayed in response to selection of a user icon or an alert icon displayed on a command center/patient manager GUI, for example. In other examples, GUI 400 may be displayed as part of a command center/patient manager UI, such as within UI 300 of FIG. 3.

As shown in FIG. 4, GUI 400 includes a name field 401 that identifies the selected patient based on name and/or or medical record number. The GUI 400 further includes an alert section 407 where patient-specific alerts are displayed. The alerts may be triggered based on information received from an EMR and/or medical devices, patient information services, and the like, as explained above with respect to FIG. 2, or triggered manually via user input. The alert section 407 may include a separate row for each individual triggered alert (which may also be referred to as a tile). In the example shown in FIG. 4, the alert section 407 is displaying a first alert 402 (which is an MRI delay alert) and a second alert 404 (which is an abnormal lab value alert). For each displayed alert, icons and/or buttons are shown that indicate that additional information may be presented that the user may view and/or otherwise interact with. For example, each alert may include a status field 406, a snooze field 408, a comment field 410, an escalate field 412, an assignment field 414, a history field 416, and a delete field 418. Each of these fields is explained in more detail below. As will be explained in more detail below, a user may set a snooze for an alert via the snooze field, leave comments about an alert via the comments field, escalate an alert via the escalate field, or take other actions on an alert. Once the user sets a snooze, enters comments, etc., the user may save/apply the actions by selecting an apply button 420. Selection of the apply button will finalize any changes made by the user. Additionally, GUI 400 includes a Cancel button 422. Selecting the cancel button will result in no changes made to the patient's alerts.

The assignment field 414 may include an assigned to box next to any row (e.g., alert) where the assign to function is possible. If the function is not available for the alert, then the assigned to box may not appear. In the example shown, the assigned to box may include a drop-down menu. Selecting the drop-down menu may prompt the user with options (e.g., care providers) configured by the local team on an alert by alert basis. User roles may limit a user to only self-assigning a task or un-assigning tasks that are assigned to them. When a selection is updated a post to the backend is immediately made and if the result is a failure then the drop down reverts to its old value. The user should be notified of failure in the standard way with the dialog (which may be red, for example) in the top of the page.

In at least some examples, each type of alert (e.g., imaging delay, abnormal test result, specific task to be performed, etc.) may be configurable at the alert level and/or at the patient level. For example, some types of alerts may not be snoozed, while other types of alerts may not be escalated. Still other types of alerts may only be resolved automatically by the command center engine. Further, some alerts may be snoozed for some patients but not others. If a given action is not available for a given alert, the corresponding icon for that action may not be displayed in the alert section. For example, if an alert for a patient cannot be snoozed, the snooze icon (e.g., the bell in FIG. 4) may not be present in the snooze field and/or the snooze field may not be present. When expanding and collapsing actions on alerts, the state of each workflow (e.g., the user input/requested action) may be remembered. In this way, if a snooze action is filled out and the user selects the escalate icon to collapse the snooze workflow and open the escalate workflow, then the snooze workflow would remain filled in until the user closes the GUI 400 (e.g., selects the apply or cancel button). This allows the user to return to the previous tab to finish work if needed. All actions are controllable at an instance level. In this way, an implementation may be able to send two alerts of the same type with different actions, e.g., snoozing and commenting on an alert. Hovering over the alert name or icon will show the same hover as is shown on the GUI 400, the style of which may vary from tile to tile. The apply button will submit the batch of changes made via the GUI 400 to the command center engine. Nothing is fully committed until the apply button is clicked. The cancel button will cancel the alert management workflow and no changes are submitted.

Thus, FIG. 4 shows an example of an alert management GUI that may be displayed within a command center/patient manager UI or as a separate display panel. The alert management GUI shown in FIG. 4 includes rows/tiles where each alert (or a subset of alerts) triggered for a selected patient are shown. For each alert, a status of that alert is shown (e.g., unresolved/not completed, in-progress, resolved/completed) as well as a priority of the alert (e.g., high or low). Further, a snooze status is shown (e.g., snoozed or not snoozed, and if snoozed, a countdown timer showing the remaining time left for the snooze). Additionally, a comment status is shown (e.g., comment available or no comment available), an escalation status is shown (e.g., escalated or not escalated), and an assigned to provider is shown. Further, various actions may be taken on each alert via the alert management GUI, such as updating the status and/or priority of an alert, adjusting the snooze (snoozing or dismissing a snooze) of the alert, adding or removing a comment for the alert, escalating or removing an escalation for the alert, adjusting the user the alert is assigned to, viewing a history of the alert, and deleting the alert. Each of these actions and each piece of information about an alert may be viewed/reached though the alert management GUI. By displaying each alert and associated user interface icons/buttons/menus that allow the information to be viewed and/or actions to be taken all on a single GUI, each alert may be managed more efficiently so that all relevant users may view actions taken on an alert and conflicting actions may be avoided. In doing so, the computing device(s) executing the command center engine and alert management engine may operate more efficiently by reducing redundant storage and reducing or eliminating redundant actions. Additional information about how alerts are triggered and alert actions are managed are provided below with respect to FIGS. 20-21B.

Figure 5:
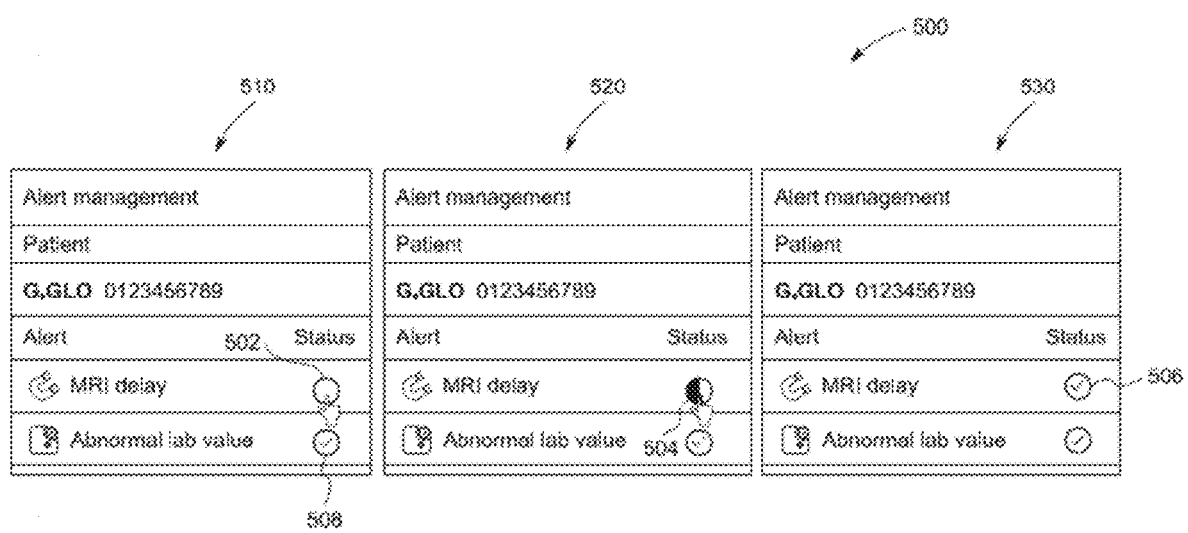
FIG. 5 shows a diagram illustrating detailed views of a section of the graphical user interface (GUI) of FIG. 4 for managing an alert status, according to an embodiment.

FIG. 5 shows partial magnified views 500 of the GUI 400 illustrating the alert status field for the alert section 407 in different states. A first view 510 shows an alert status button 502 for the first alert in a first, incomplete state. When the user selects the alert status button 502, the alert status transitions to an in-progress state, which is shown by the alert status button 504 in view 520, with a half-filled circle. When the user selects the alert status button 504 (e.g., the "in-progress" state), the alert status may transition to the "complete state" shown by alert status button 506 in the view 530. In some examples, the status of an alert may be set automatically, such as the state shown in by alert status button 508 of view 510, showing a circle with a checkmark that may have a different visual appearance than the alert status button 506 (e.g., the alert status button 506 may be a first color, such as green, while the alert status button 508 may be a second color, such as blue). In this way, a user selecting the alert status button 502 a first time results in the circle changing from an "open circle" to a "half-circle" signifying that the status has changed from "Incomplete" to "In-progress". The user selecting the alert status button a second time results in the circle changing from the "half-circle" to a "whole-circle" with a checkmark inscribed within the circle, signifying the status has changed from "In-progress" to "Complete". The user selecting the alert status button a third time results in the circle changing from the "whole-circle" with a checkmark inscribed within the circle back to "Incomplete" state.

If an alert instance does not use all the status values, then it will advance to the next value. Thus, if In Progress is not enabled then the click would go from incomplete to complete. If no action can be taken on a status manually, then clicking on the circle will not make any impact. This is controlled on an alert by alert basis. An example of this is that auto-completed tasks cannot be manually uncompleted on the GUI 400. The alert status may be completely disabled on a row by row basis depending on user preference or alert configuration. If the alert status is completely disabled for an alert, then the circle does not appear and the column for status also does not appear. If the status workflow is not editable then a special icon such as x may be shown, regardless of the status of the workflow.

Referring back to FIG. 4 and specifically the snooze field, if an alert is not currently snoozed then the bell icon is faded without any Z's next to it (as shown for the first alert). If the alert is currently snoozed, then the bell icon is lit up and remaining time of the snooze is displayed (e.g., in parenthesis in the format of #T #T #T) as shown for the second alert or "Indefinite" if the snooze is untimed. The clock may tick in real time. When the PC clock advances one minute then the duration should update to reflect the movement of time. The icon for the bell may not appear at all if the alert cannot have any snooze actions taken.

Thus, two states of the snooze functionality are shown by a first snooze icon associated with the first alert and a second snooze icon associated with the second alert. The first snooze icon has a first visual appearance (e.g., grayed out/faded) to indicate that the snooze function is inactivated for the first alert, while the second snooze icon has a second, different visual appearance (e.g., white) to shows that the snooze function is activated for the second alert. When a snooze is activated, the area next to the snooze button will display a countdown timer. Selecting a snooze icon, such as the first snooze icon, will expand display of the sub-menu shown in FIG. 6.

Figures 6, 7:
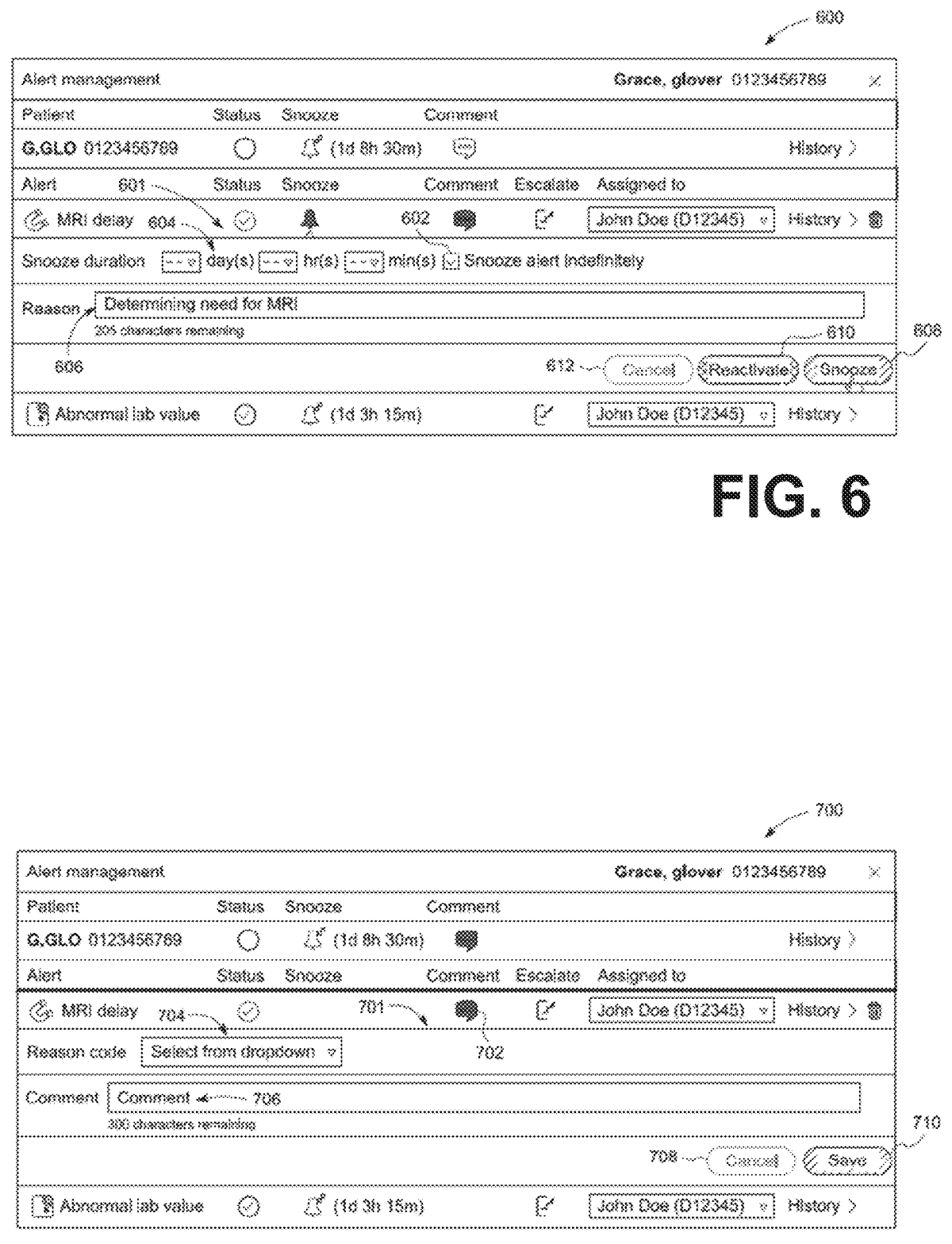

FIG. 6 shows a view 600 of the GUI 400 including a snooze sub-menu 601 in an expanded state. The snooze sub-menu 601 includes several fields via which a user may set or adjust a snooze for a selected alert (e.g., the alert associated with the selected snooze icon), outlined below. The snooze sub-menu 601 includes a snooze alert indefinitely button 602. Selecting the snooze alert indefinitely button 602 allows the user to snooze the alert indefinitely.

The snooze sub-menu 601 includes a snooze duration menu 604 which allows the user to input a duration of the snooze functionality for the selected alert. In the depicted example, the snooze duration menu 604 includes a plurality of drop-down menus which via which the user may denote the duration of the alarm (e.g., days, hours, minutes menus). In other examples, the snooze duration menu 604 may include text boxes via which each time field may be specified. The snooze sub-menu 601 may further include a reason text input area 606, which may only appear when the applied user action is to "snooze" an alert or "dismiss" a snoozed alert. Via the reason text input area 606, the user may enter text in a free form text field, and save the generated data within the alert.

The snooze sub-menu 601 further includes a snooze button 608, a reactivate button 610, and a cancel button 612. By selecting the snooze button 608, the snooze functionality (e.g., as specified by the user via the snooze sub-menu) will become enabled, and the sub-menu will collapse back to the GUI 400 of FIG. 4. In some examples, enabling the snooze functionality will simultaneously begin the countdown timer displayed in the as part of the snooze icon for that alert (such as the countdown timer associated with the snooze icon for the second alert 404). The snooze button 608 may only be selected when the workflow is completed by the user, until then, it remains unusable. The reactivate button 610 may only be activated when the snooze functionality is enabled. In some examples, selecting the reactivate button 610 clears the prior snooze settings for the alert and thereby cancels the snooze (e.g., reactivates the alert). In some examples, selecting the reactivate button 610 simultaneously collapses the sub-menu back to the GUI 400 of FIG. 4. Selecting the cancel button 612 may collapse the sub-menu and return the user back to the GUI 400 of FIG. 4 without changing the settings for the snooze for the alert. In some examples, selecting the snooze button 608 will collapse the menu back to the GUI 400 of FIG. 4.

In some examples, the values in the fields of the snooze sub-menu 601 may be populated with the configured defaults for the alert, and the user may edit the snooze settings to differ from the configured defaults, if desired. If there are multiple alerts involved in the interaction, then the defaults may be left blank. This includes if check boxes are used in a multi-alert management to select only one alert. Once a user has selected a snooze duration, the duration field/menu may no longer automatically update. On some views, such as a mobile view, a selection wheel may be presented and free input may not be allowed. The validation performed on duration should be greater than 0 minutes and less than the maximum value set in the configured default settings.

A snoozed alert will have its timer reset if the snooze action is applied to it again. The following list describes what should happen based on the alert's current state and updated state, where an active state is an alert that is not snoozed: if a current state is active, a reactivate action results in no action; if a current state is active, a timed snooze action results in an alert snoozed for a duration; if a current state is active, an indefinite snooze action results in the alert snoozed indefinitely; if the current state is snoozed, a reactivate action results in the alert being activated; if the current state is snoozed, a snooze action results in the alert being snoozed for a new duration; if the current state is snoozed, an indefinite snooze action results in the alert being snoozed indefinitely; if the current state is indefinite snooze, a reactivate action results in the alert being activated; if the current state is indefinite snooze, a snooze action results in the alert snoozed for the specified duration; if the current state is indefinite snooze, an indefinite snooze action results in no action. The snooze workflow may be validated to ensure that a snooze duration is provided, and further that a reason is provided for snoozing the alert.

Briefly referring back to FIG. 4, GUI 400 includes the comment field 410 where a comment icon may appear next to any row (e.g., alert) where the comment function is possible. Clicking on the comment icon will open an expanded comment sub-menu 701 shown in FIG. 7 to enable a comment workflow for commenting on the alert. If the function is not available for the row, then a comment icon will not appear. Therefore, the appearance of this icon is dynamic. The header may be a comment icon with a tool tip that is defaulted to "Comment" and may be customizable as needed.

FIG. 7 shows a view 700 of GUI 400 with the comment sub-menu 701 in an expanded state, according to an embodiment. When expanded to show the comment sub-menu 701, the comment icon 702 may still appear. Selecting the comment icon 702 a second time collapses the sub-menu. The comment sub-menu 701 includes a reason code menu 704, which may be a drop-down menu that displays pre-set reasons for setting the comment. The pre-set reasons may be configurable based on the type of alert (e.g., an imaging delay alert may have a first set of pre-set reason codes and an abnormal lab value alert may have a second set of pre-set reason codes). If the reason code drop-down option is not turned on for the alert, then the reason code menu 704 will not appear. The reason code is separate from the comment and should be stored and managed entirely separately. The comment sub-menu 701 further includes a comment field 706. The comment field 706 may be a free form text field that accepts any user text. Its default text should be "Comment" this can be configured in the metadata set for the alert. The default text may act as a prepopulated start to the comment or the default text may go away when the user starts to enter a comment. The comment field 706 is configurable at a task instance level to turn on or off (e.g., each alert type may be configured to allow or not allow comments). If disabled, the entire row should not appear.

The comment sub-menu 701 includes a cancel button 708 and a save button 710. The cancel button 708, when selected, causes the sub-menu to collapse the workflow without taking any action and resets all fields for the comment workflow to their default state for the alert. The save button 710 may be unselectable until the comment workflow is completed. Once a validated reason code and/or comment have been entered, then the save button 710 may be selectable. In some examples, once a user starts to enter text into the comment field 706, a prepopulated comment may be predicted from the text and entered into the comment field 706, and the user may accept the prepopulated comment entering a suitable command (e.g., selecting the enter key on a keyboard) or reject the prepopulated comment.

Referring briefly back to FIG. 4, the GUI 400 includes the escalate field 412 where an escalation icon may be shown for each alert. For example, an escalation icon may be displayed next to any row (e.g., alert) where the escalate function is possible. In the example shown in FIG. 4, each alert can be escalated, and thus an escalation icon is displayed for each alert. The escalation icon for the first alert is faded (e.g., indicating that the first alert has not been escalated), while the escalation icon for the second alert is lit up (e.g., indicating that the second alert has been escalated). Selecting an escalation icon will open an escalation sub-menu, as shown in FIG. 8.

Figures 8, 9, 10:
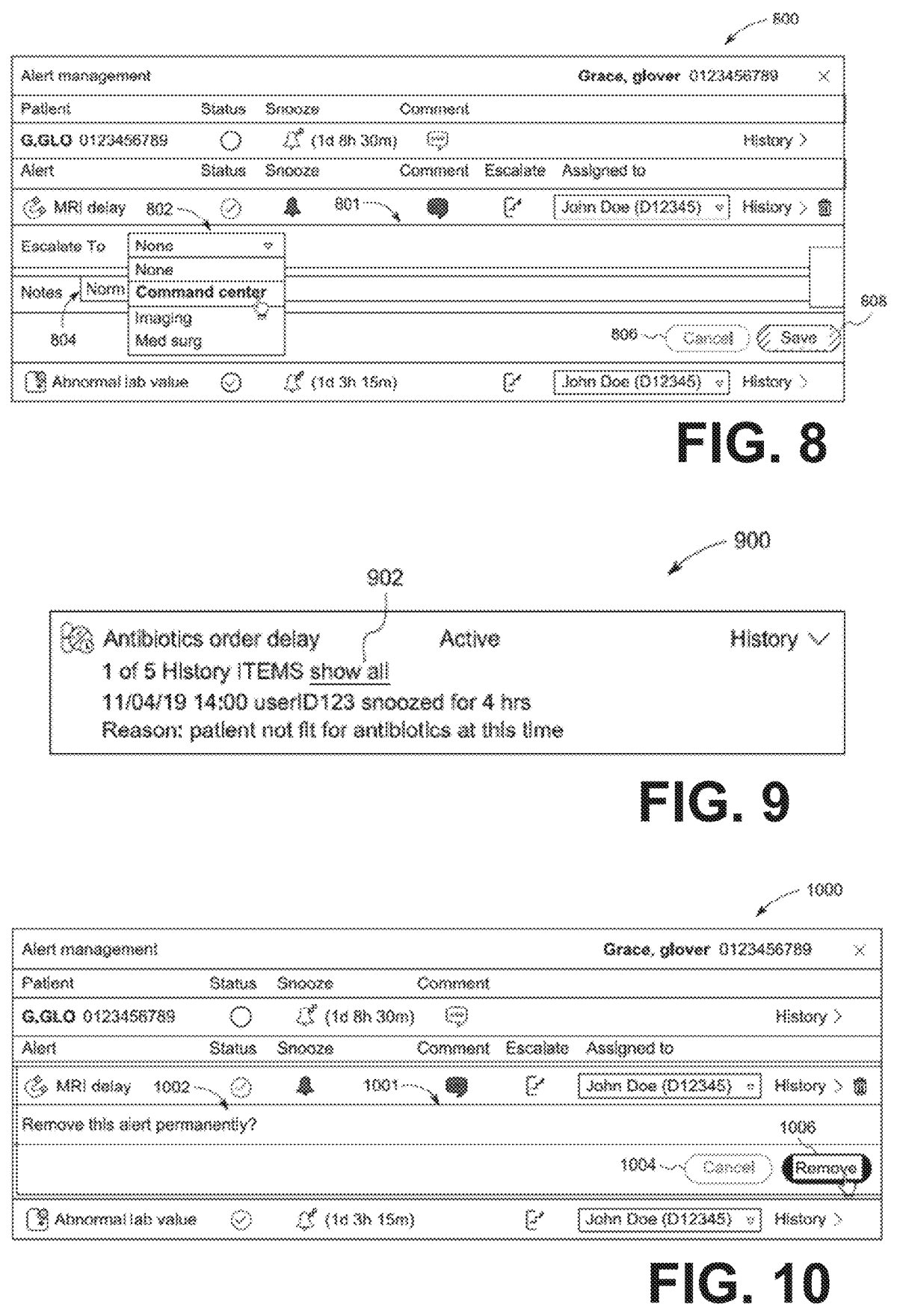

FIG. 8 shows a view 800 of GUI 400 with the escalation sub-menu 801 in an expanded state, for managing an alert escalation, according to an embodiment. The escalation sub-menu 801 includes an escalate to menu 802, which may display pre-defined options for the user to select from a drop-down menu, for example. The pre-defined options may include care provider groups, hospital units/wards, or other groups at the hospital (e.g., diagnostic imaging), as well as the command center or patient manager. Selection of one of the pre-defined options may result in the alert being escalated to the selected group. For example, the selected group may receive a notification about the escalated alert. In some examples, the alert may be visualized as escalated only to the selected group. For example, when the command center is selected, the alert may be escalated on all UIs generated by the command center engine, so that all care providers may see the escalated status. Selecting imaging, for example, may instead escalate the alert only for UIs viewed by the imaging group.

The escalation sub-menu 801 may include a notes section 804 which includes a free-form text field where the user may include notes about the patient (e.g., a reason for the escalation). The escalation sub-menu 801 further includes a cancel button 806 and a save button 808, where selection of the cancel button 806 collapses the sub-menu without applying or saving any of the collected user inputs and selection of the save button 808 applies the escalation and collapses the sub-menu.

FIG. 9 shows a diagram illustrating an history panel 900 for managing an alert history in an expanded state, which may be displayed upon a user selecting a history button displayed as part of GUI 400 (e.g., a history button for an alert displayed as part of the history field 416), according to an embodiment. The history panel 900 may display some or all of history of actions taken regarding the selected alert, which in the present example is an "antibiotics order delay" alert. A summary of the history items may appear at the top of the list. When opened for the first time, only the most recent history item is shown. The display text is dynamic and may display # of N HISTORY ITEMS. The first line may show the action taken in the form of [DateTime of Event]+[User Name]+[Action]. For example, the action shown in FIG. 9 is a user-initiated snooze of the alert. The next line may display the canned reason code from a comment if applicable (e.g., patient not fit for antibiotics). The next line may display "Comment:"+[DelayReason]. The [DelayReason] may come from the reason entered by the user when taking the action. This also applies to escalation comments and notes. The Show All button 902 may expand (if selected) to show all of the history items. This action is always show all regardless of the number of history items present. When selected, the number of alerts should update to say "N of N HISTORY ITEMS" where N is the total number of history items. The "Show all" text also changes to say "Collapse".

FIG. 10 shows a view 1000 of the GUI 400 with a delete sub-menu 1001 in an expanded state, for managing an alert deletion, according to an embodiment. The delete sub-menu may be displayed in response to selection of an icon in the delete field 418 (e.g., a trashcan icon). If an alert is not able to be deleted, an icon will not be present for that alert in the delete field. The delete sub-menu 1001 includes a default confirmation dialog box 1002, which defaults to displaying "Remove this alert permanently?" or other suitable text. The cancel button 1004, when selected, closes the delete sub-menu/workflow without taking any action. The remove button 1006, when selected, will permanently remove the alert. Once the alert is removed/deleted, the sub-menu collapses back down and the alert is no longer visible in alert manager or the GUI 400.

Thus, FIGS. 4-10 illustrate an alert manager GUI that may display alerts that have been triggered for a selected patient, and various sub-menus that may be displayed via the alert manager GUI in order to take various actions regarding selected alerts, such as snooze, comment, escalate, etc. The manner in which the information is presented in FIGS. 4-10 is exemplary and non-limiting. The alerts described herein may be displayed in other forms without departing from the scope of this disclosure. FIGS. 11 and 12 show example GUIs that may be displayed as panels within a command center/patient manager GUI (e.g., GUI 300) or that may be displayed in response to user selection of an appropriate element from a command center/patient manager GUI.

FIG. 11 shows a diagram illustrating an example graphical user interface 1100 for managing an alert status in a single alert per patient format, according to an embodiment. GUI 1100 includes two alerts, a first alert for a first patient and a second alert for a second patient (more patients may be included without departing from the scope of this disclosure). The first alert is active, depicted via a first visual appearance (e.g., white, bright). If an alert is in the active status then the alert may appear as it would on the patient manager (e.g., on GUI 400). The second alert is snoozed, depicted via a second visual appearance (e.g., faded). If an alert is in the snoozed state, then a translucent fade may be applied to the entire alert to indicate that it is snoozed. In GUI 1100, the time since the alert was triggered is also shown, along with patient location.

FIG. 12 shows a diagram illustrating an example graphical user interface 1200 for managing an alert status in a multiple alerts per patient format, according to an embodiment. GUI 1200 is also referred to as a badge and includes a row for each of seven patients, though more or fewer patients may be shown without departing from the scope of this disclosure. If any number of alerts are snoozed on a multi-alert patient badge but not all alerts, then the entire badge will appear active. The individual alerts that are snoozed will appear translucent. If all the alerts on a badge are snoozed, then the entire patient badge will appear snoozed. This applies for a multi-alert badges even if only one alert is present on the patient.

For each patient, GUI 1200 displays a time since initial concern, patient information, delayed actions, and patient location. The delayed actions may be depicted via icons that convey which actions have been delayed (e.g., delayed lab test, delayed imaging exam, delayed prescription order). The delayed actions may be examples of alerts and thus may be triggered as explained previously.

FIG. 13 shows a diagram illustrating example graphical user interface 1300 for conveying an integrated alert status, according to an embodiment. The GUIs 1300 include an in-progress icon to convey that the alert status is in-progress (and other alert statuses may be conveyed in a similar manner). The first GUI includes a comment icon that may only appear when a comment is submitted for the alert. The comment icon may be replaced by an escalation icon if an alert is both commented and escalated. A bar on the left hand side of the GUI may be present if the alert is assigned to the current user. An escalation icon may appear if a task is escalated, as shown in the third GUI. The icons of the GUIs are typically not hoverable; any hover needs are rolled into the alerts hover.

FIG. 14 shows a view 1400 of GUI 400 illustrating example alert priority states, according to an embodiment. The alert priority status indicator may have three different states. These states or modes are configurable at various different levels. The states include Not Priority state depicted by an open clear circle with an exclamation point, and a Priority state depicted by a solid circle with an exclamation point. In some examples, the solid circle may be red in color to indicate the high priority status. On selecting the priority icon, the icon will toggle between priority and not priority. The priority concept can be completely disabled on an alert level basis if desired. If the alert priority status concept is completely disabled, then the circle does not appear and the column for status also does not appear.

FIG. 15 shows a diagram illustrating an example graphical user interface 1500 for depicting alert information upon hovering, according to an embodiment. For example, GUI 1500 may be displayed when a user hovers over an alert in a command center/patient manager interface (e.g., GUI 300 or GUI 400) or other suitable element. Comments on a patient may be shown in a comment section 1502. Reason codes can also be displayed as needed in a similar format. Escalation comments may appear in the hover in their own section, e.g., escalation section 1504. If a hover is for a snoozed entity the top bar should put the snooze icon and duration in the top bar, as shown at 1506. If a hover has a status for the entire entity the top bar should show an icon of its status. The person assigned to the entity can be shown in the hover in its own section, e.g., assigned to section 1508. Alerts listed within a single badge may have four icons to indicate status, active snooze, comment, and escalation, as shown at 1510. Hovering over should show a hover of the comment with a header of who made the comment and when. The icons only appear if active for snooze, comment, and escalate. A snooze alert may have a translucent fade over it. Snooze comments appear in the hover in their own section, e.g., snooze section 1512.

Figure 17:
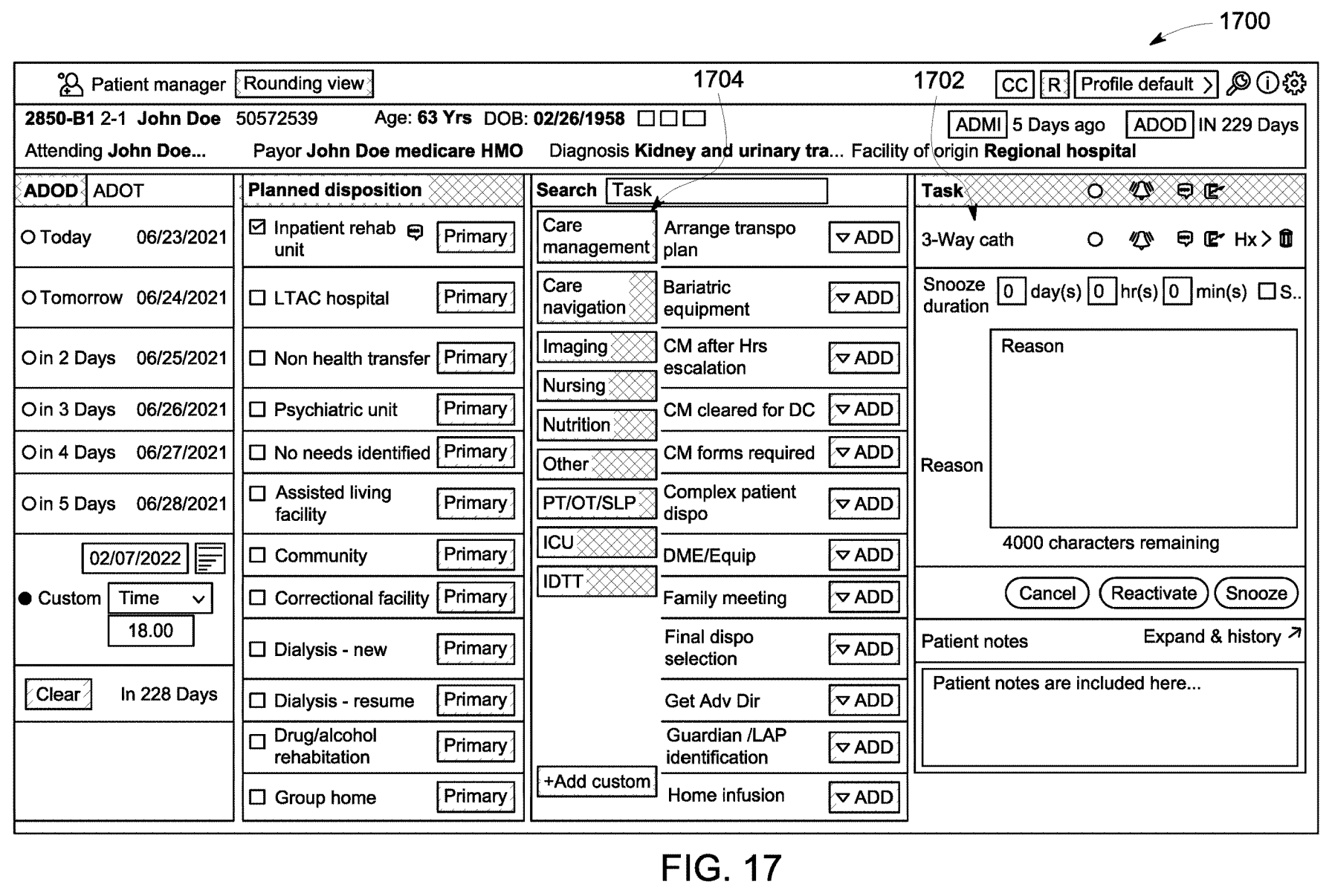

FIGS. 16 and 17 illustrate an alternative view for a command center/patient manager GUI 1600, such as a rounding view. Information pertaining to a single selected patient is shown. GUI 1600 includes a task section 1602 where alerts (which may also be referred to as tasks) for the patient are displayed. As explained above with respect to FIGS. 4-10, each alert may be depicted in a respective row, and information about each alert may be conveyed via icons indicating alert status, snooze status, comment status, escalation status, history, and delete, each displayed on the same, single interface. Each icon may be selected to cause a respective sub-menu to be displayed, similar to the sub-menus described above. For example, selecting a snooze icon will cause a snooze sub-menu to be displayed, selecting an escalation icon will cause an escalation sub-menu to be displayed, etc. The visual appearance of each icon may convey whether that action is inactive or active. For example, two alerts are currently escalated, indicated by the escalation icon for each of the two alerts (e.g., Bariatric Equipment and Post DC FU Appt) being brighter/having a different color than the other escalation icons.

FIG. 17 shows the GUI 1600 with a snooze sub-menu 1702 for a first alert (e.g., 3-Way Cath) expanded. The snooze sub-menu 1702 may be the same as snooze sub-menu 601 of FIG. 6, and thus the description of snooze sub-menu 601 likewise applies to snooze sub-menu 1702. As appreciated from FIG. 17, the various sub-menus described herein may be displayed within a larger command center/patient manager GUI with additional information about the patient displayed, including a panel 1704 where new tasks/alerts may be triggered via user input (referred to as manual alerts).

Figure 18:
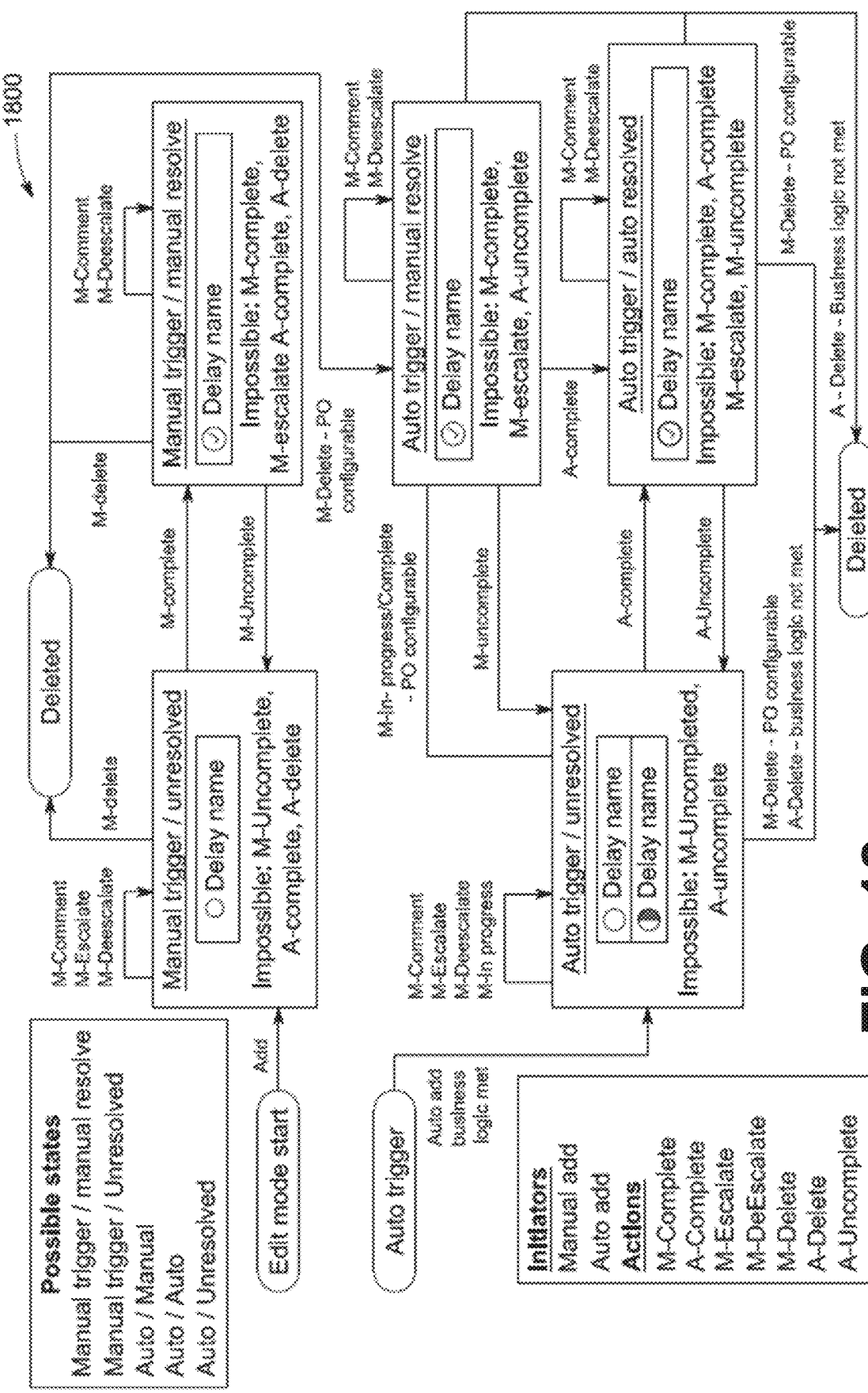
FIG. 18 shows a block diagram illustrating an example method for determining a status of an alert based on automatic and manual triggering, according to an embodiment.

FIG. 18 shows a block diagram illustrating an example method 1800 for determining a status of an alert based on automatic and manual triggering, according to an embodiment. As depicted, possible alert states include manual trigger/manual resolve, manual trigger/unresolved, automatic trigger/manual resolve, automatic trigger/automatic resolve, automatic trigger/unresolved, and automatic confirmation. An alert may be initiated by a manual add or an automatic add. Actions on alerts may include manual complete, automatic complete, manual comment, manual uncomplete, manual delete, and automatic delete. Different actions are available for managing an alert based on the state of the alert. For example, if the state of an alert is manual trigger/unresolved, actions that may be performed include manual comment, manual escalate, manual deescalate, manual complete, manual delete, while actions that may not be performed are manual uncomplete, automatic complete, automatic delete. If the state is manual trigger/manual resolve, the actions may include manual delete, manual comment, manual deescalate, manual uncomplete, while actions that may not be performed include manual complete, manual escalate, automatic complete, and automatic delete. If the state is automatic trigger/manual resolve, the actions that may be performed include manual delete, manual comment, manual deescalate, manual uncomplete, and automatic complete, while actions that may not be performed include manual complete, manual escalate, and automatic delete. If the state is automatic trigger/automatic resolve, the actions may include manual comment, manual deescalate, manual delete, while actions that may not be performed include manual complete, automatic complete, automatic delete, manual escalate, and manual uncomplete. If the state is automatic trigger/unresolved, the actions that may be performed include manual comment, manual escalate, manual deescalate, manual complete, automatic complete, manual delete, and automatic delete, while the actions that may not be performed include manual uncomplete. Manual triggers result from a user entering an edit mode of the alert management engine 202 and manually adding an alert. Automatic triggers result from the alert management engine 202 automatically determining that one or more criteria or rules are satisfied by EMR signals, for example, or other signals relating to a patient.

FIG. 19 shows a diagram illustrating an example graphical user interface 1900 for a patient downgrade status module, according to an embodiment. As depicted, the downgrade readiness of patients (e.g., Ready for Downgrade, Possible Downgrade, and Not Eligible) may be determined and displayed via the graphical user interface 1900 based on criteria and/or alerts. GUI 1900 may be a different view of GUI 300, e.g., a downgrade expediter view that highlights information pertaining to downgrade readiness for downgrading patients to be discharged or moved to a different unit.

Figure 20:
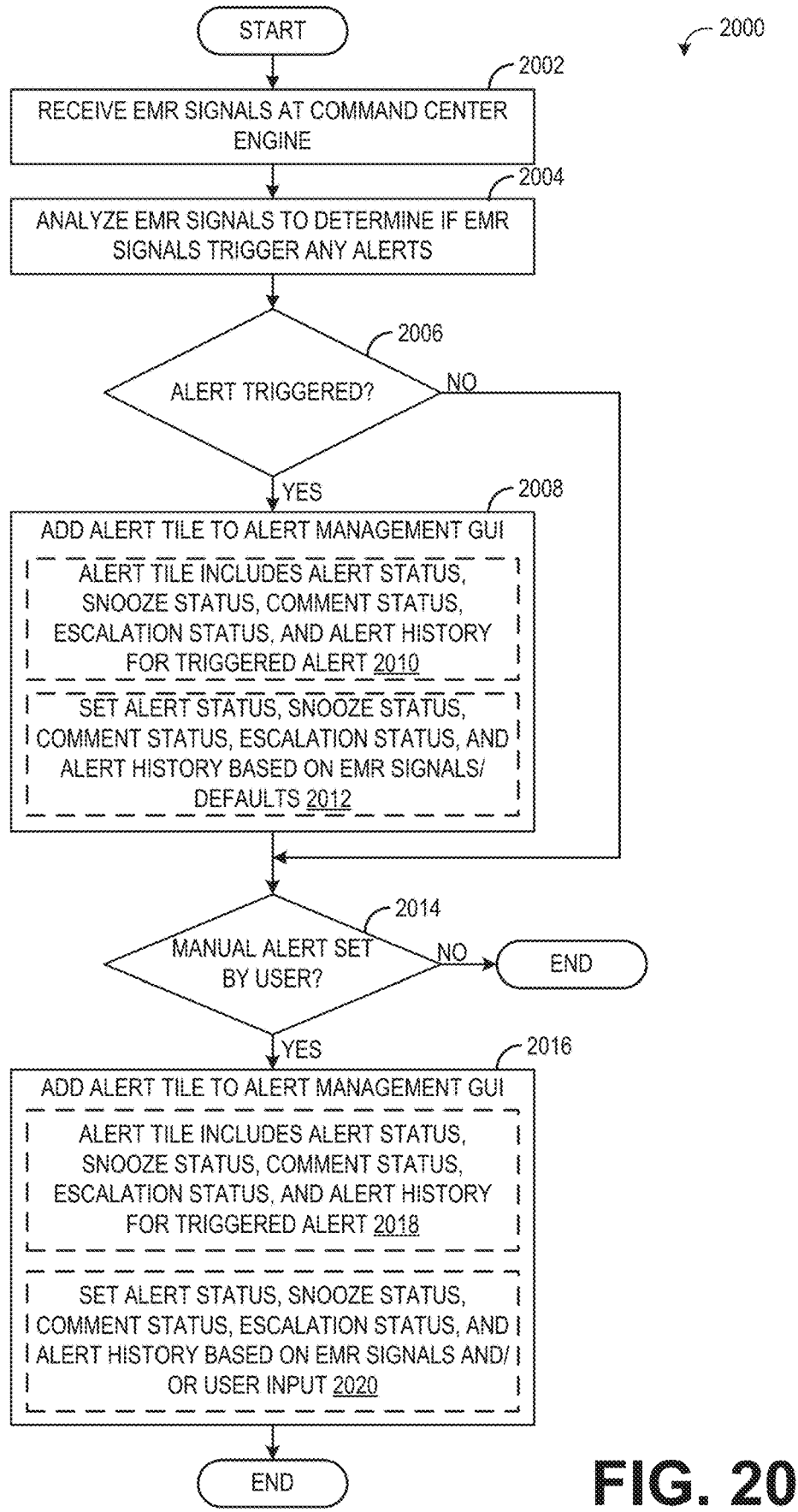
FIG. 20 is a flow chart illustrating a method for generating and displaying alert tiles, according to an embodiment.

FIG. 20 is a flow chart illustrating a method 2000 for triggering and displaying an alert, according to an embodiment of the disclosure. Method 2000 may be carried out according to instructions stored in memory of a computing device and executed by one or more processors of the computing device, such as computing device 102 of FIG. 1. As explained above, the computing device 102 may include a command center engine 140 that receives signals from an EMR database (e.g., EMR database 280), analyzes the signals, and triggers alerts via alert management engine 142 and/or alert management engine 202, which are then displayed via an appropriate GUI, such as UI 300, GUI 400, and/or GUI 1600.

At 2002, EMR signals are received at the command center engine. The EMR signals may include information about one or more patients being treated at a specific medical facility or medical network. The EMR signals may include information regarding patient vital signs/monitored patient parameters, provider-ordered medications, lab tests, diagnostic imaging exams, and procedures, treatment guidelines/protocols, lab test results, diagnostic imaging results, current prescriptions and prescription status, scheduled procedures, and so forth.

At 2004, the received EMR signals are analyzed to determine if the EMR signals have triggered any alerts. As explained above with respect to FIG. 2, the alert management engine may include a rules module that applies rules to the received EMR signals to determine if the EMR signals have triggered any alerts. Each alert may relate to a task for caring for a patient, and thus may include alerts relating to reminders or delays in scheduling or performing procedures and/or exams, ordering medications, ordering lab tests, receiving ordered medications, receiving lab test results, etc. The alerts described herein may not include specific monitoring device-based alerts such as alerts that are issued when a patient's blood pressure rises above a threshold or when a patient's oxygen saturation drops below a threshold, which may be handled in a different manner due to the time-sensitive nature of such alerts.

At 2006, method 2000 determines if any alerts have been triggered based on the received EMR signals. If no alerts have been triggered, method 2000 proceeds to 2014, which is described below. If one or more alerts have been triggered, method 2000 proceeds to 2008 to add an alert tile to an alert management GUI. As indicated at 2010, the alert tile may be specific for one triggered alert for a patient, and may include an alert status, a snooze status, a comment status, an escalation status, and an alert history for the triggered alert, each of which may be set based on the EMR signals and/or configured defaults (as indicated at 2012). Further, as time progresses and additional EMR signals are obtained after the initial alert is triggered, each status may be updated when appropriate (as will be explained in more detail below with respect to FIGS. 21A and 21B). Further still, a separate alert tile may be generated for each alert that is triggered. FIG. 4 shows example alert tiles that may be generated according to the process of method 2000, such as the row for the first alert 402 and the row for the second alert 404.

At 2014, method 2000 determines if any manual alerts have been set by a user. For example, a user may define an alert for a given patient or set of patients via interaction with a command center interface, or other suitable mechanism. The user may specify the alert type and configure the permissions, default settings, and so forth, which may be saved and applied to trigger an alert. If a manual alert is set by a user, method 2000 proceeds to 2016 to add an alert tile to the alert management GUI for the manually-set alert. The alert tile may be specific for one manually-set alert for a patient, and may include an alert status, a snooze status, a comment status, an escalation status, and an alert history for the triggered alert, as indicated at 2018, each of which may be set based on the EMR signals and/or user input (as indicated at 2020). In this way, when a patient manager GUI and/or alert management GUI for a given patient is displayed, any alerts, whether alerts that triggered automatically or alerts that are set manually, are shown via the corresponding alert tile. Method 2000 then ends.

Figure 21A:
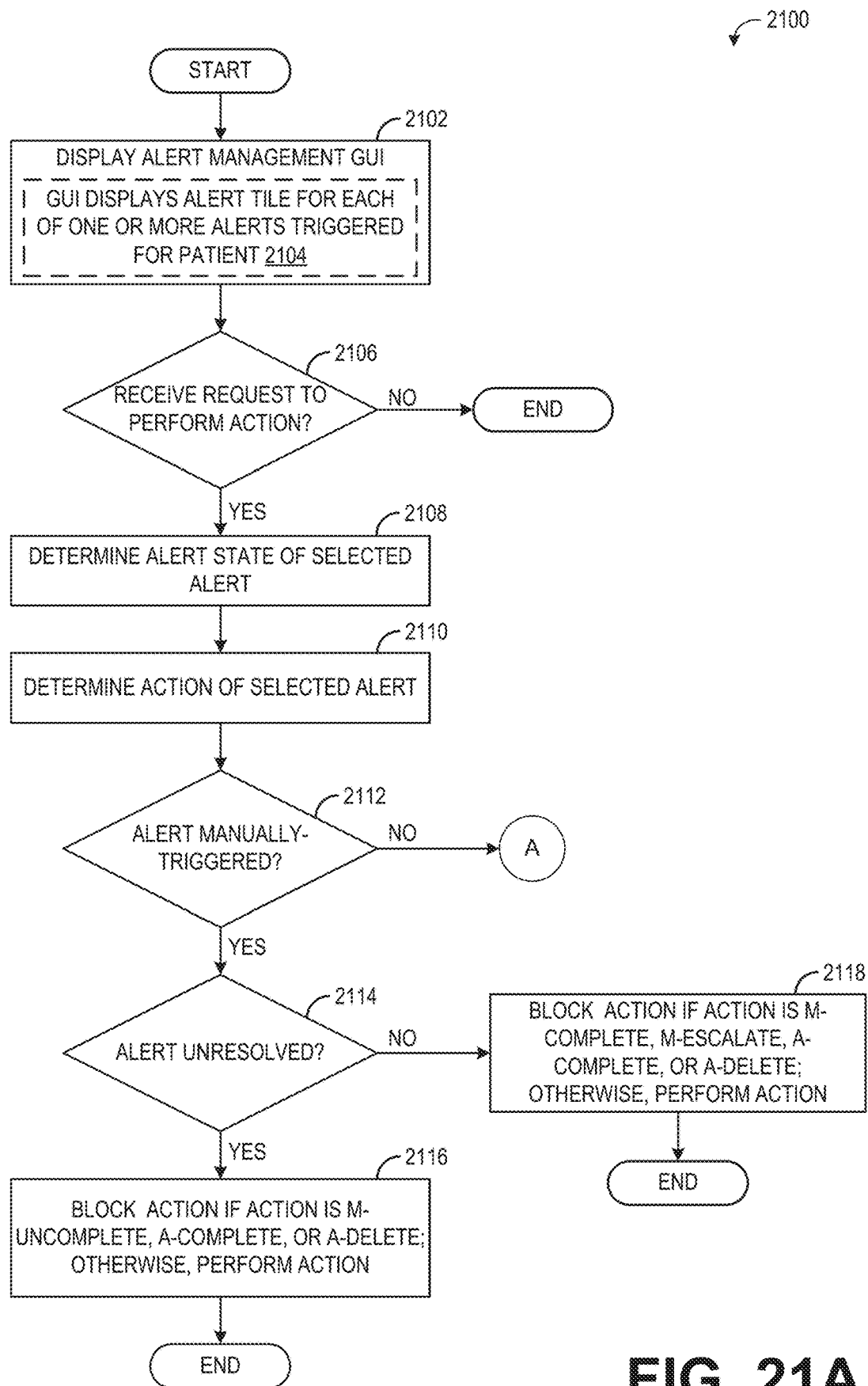
FIG. 21A and FIG. 21B show a flow chart illustrating a method for performing requested alert actions, according to an embodiment.
Figure 21B:
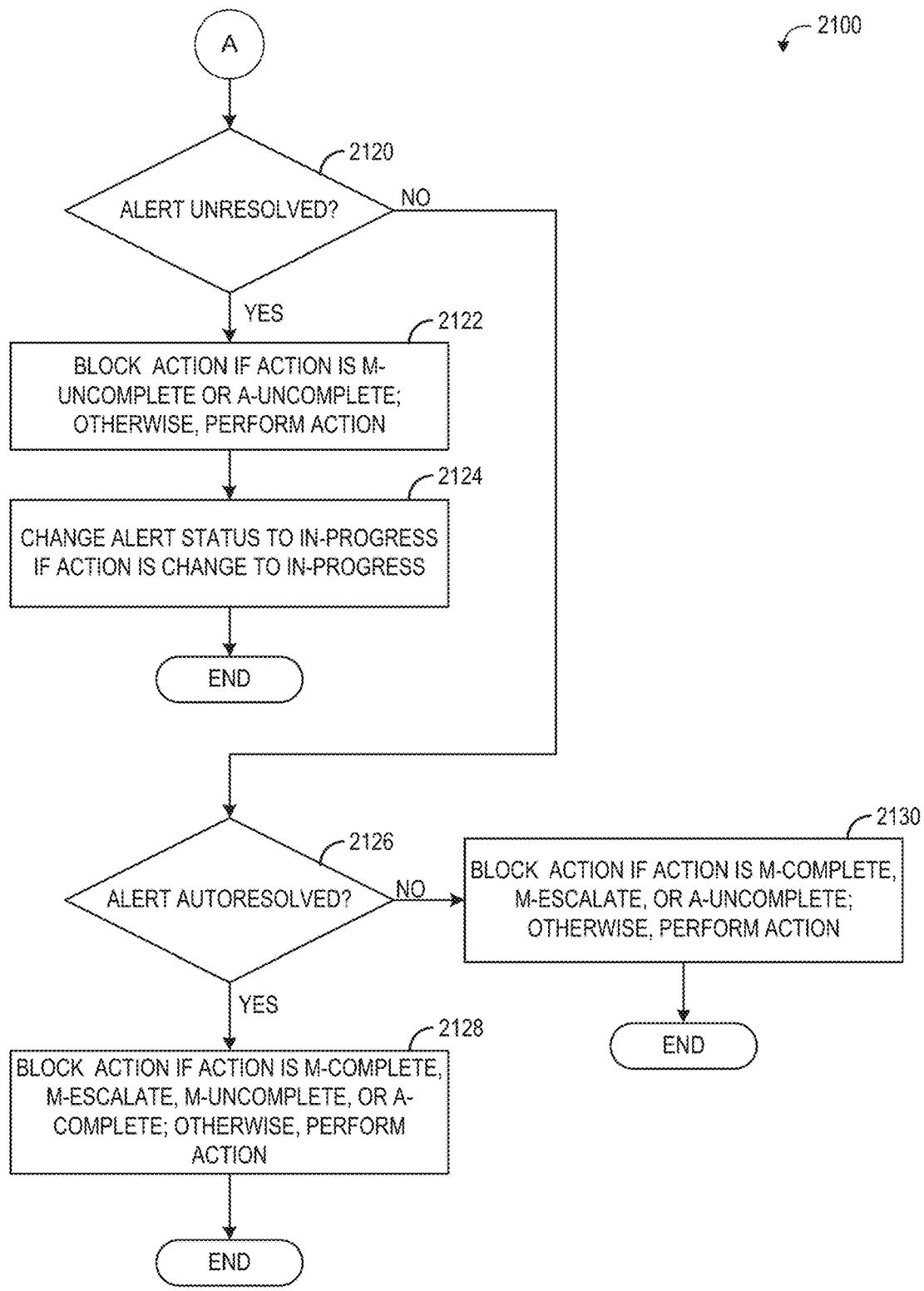

FIGS. 21A and 21B are a flow chart illustrating a method 2100 for managing alert actions, according to an embodiment of the disclosure. Method 2100 may be carried out according to instructions stored in memory of a computing device and executed by one or more processors of the computing device, such as computing device 102 of FIG. 1. Method 2100 may apply a set of rules to determine if requested alert actions are permissible and then block or allow actions as permissions dictate, which may be determined based on the process shown by the block diagram of FIG. 18.

At 2102, an alert management GUI is displayed, which includes an alert tile for each of one or more alerts triggered for a patient, as indicated at 2104. The alert management GUI may be similar to the GUI 400 of FIG. 4 and may be displayed as a module within a patient manager GUI, such as UI 300 or GUI 1600 or as a separate display panel. The alert tiles within the alert management GUI may be generated as explained previously with respect to FIG. 20.

At 2106, method 2100 determines if a request to perform an action on an alert has been received. The request may be received via user input applied to the alert management GUI. For example, as explained above with respect to FIGS. 4-10, a user may request an action, such as snoozing an alert, escalating an alert, deleting an alert, etc., by selecting one or more user interface buttons, entering information into one or more text fields, etc., of the alert management GUI. When the requested action is received via user input to the alert management GUI, the action may be classified as a manual action. In some examples, the requested action may be an automatic action that is triggered by the command center engine/alert management engine based on EMR signals. For example, if a certain amount of time has elapsed since an alert was initially triggered, the alert may be automatically escalated. In another example, if the EMR signals indicate that an alert has been resolved (e.g., lab test results are received for an alert indicating that the lab test results were delayed), the alert may be automatically marked as complete or resolved.

If no request to perform an action is received, method 2100 ends. If a request to perform an action is received, method 2100 proceeds to 2108 to determine the alert state of the selected alert (e.g., the alert to which the received action pertains). The alert state may indicate whether the alert was automatically or manually triggered. The alert state may also indicate whether the alert is currently resolved (e.g., has an alert status of complete) or unresolved (e.g., has an alert status of incomplete), and if the alert is resolved, if the alert was manually or automatically resolved. Thus, possible alert states include manual trigger/manual resolve, manual trigger/unresolved, automatic trigger/manual resolve, automatic trigger/automatic resolve, automatic trigger/unresolved, and automatic confirmation. At 2110, the action of the selected alert is determined (e.g., the requested action to be performed on the alert). Possible requested actions include manual complete, automatic complete, manual comment, manual uncomplete, automatic uncomplete, manual delete, automatic delete, manual escalate, and manual de-escalate. Method 2100 includes the application of rules to avoid conflicts in requested actions, and thus is directed to managing actions that can conflict with other actions. However, it is to be appreciated that the request may include a request to perform another action (not listed above), such as view an alert history.

At 2112, method 2100 determines if the alert is a manually-triggered alert. If the alert is not a manually-triggered alert, the alert is an automatically-triggered alert, and method 2100 proceeds to 2120 of FIG. 21B, which is described below. If the alert is a manually-triggered alert, method 2100 proceeds to 2114 to determine if the alert state is currently unresolved (e.g., the alert status is incomplete). If the alert is unresolved, method 2100 proceeds to 2116 to block the requested action if the requested action is a manual uncomplete (M-uncomplete), an automatic uncomplete (A-uncomplete), or an automatic delete (A-delete), otherwise the action is performed. An M-uncomplete action may include a user selecting a status button for the alert to attempt to revert the status to uncomplete. Likewise, an A-uncomplete may include the alert management engine attempting to revert the status to uncomplete. However, since the alert status is already incomplete/unresolved, the user (or alert management engine) may not even be given the option of performing an uncomplete. An A-delete may include the alert management engine attempting to delete the alert (e.g., due to EMR signals indicating the alert has been resolved and is no longer relevant). In this way, when the selected alert is manually triggered (e.g., set by a user) and is currently unresolved, the selected alert cannot be reverted from completed to uncompleted (because the status is currently unresolved), and cannot be automatically deleted by the alert management engine, even if the EMR signals indicate the alert is no longer relevant. That is, if an alert is manually triggered, the alert can only be deleted by a user and cannot be deleted automatically. Allowed actions for a manually-triggered, unresolved alert include manual comment, manual escalate, and manual de-escalate, each of which may maintain the status of the alert. Additional allowed actions may include manual complete, which changes the alert status to resolved, and manual delete, which deletes the alert (and causes the alert tile for that alert to no longer be displayed). Method 2100 ends.

If at 2114 method 2100 determines that the selected alert is not unresolved (e.g., the alert is resolved/has a status of being complete), method 2100 proceeds to 2118 to block the requested action if the action is a manual complete (M-complete), a manual escalate (M-escalate), an automatic complete (A-complete), or an A-delete, otherwise, the requested action is performed. Again, because the alert is manually-triggered, it cannot be automatically deleted. Further, because the alert has been marked complete/has been resolved (e.g., the status of the alert is complete), the alert cannot be marked complete (and marking the alert as complete may not be presented as an option) and cannot be manually escalated. In this way, accidental requests such as escalating an alert that is already completed may be avoided, which may reduce healthcare provider burden and limit alarm fatigue as well as efficiently use system resources. Allowed actions for a manually-triggered, resolved alert include manual comment and manual de-escalate, each of which may maintain the status of the alert. Additional allowed actions may include manual uncomplete, which changes the alert status back to unresolved, and manual delete, which deletes the alert (and causes the alert tile for that alert to no longer be displayed). Method 2100 ends.

Referring to FIG. 21B, method 2100 continues from 2112 to 2120 when the selected alert is an automatically-triggered alert, where method 2100 determines if the selected alert is currently unresolved. If the selected alert is not currently unresolved, method 2100 proceeds to 2126, which is discussed below. If the selected alert is currently unresolved, method 2100 proceeds to 2122 to block the requested action if the action is an M-uncomplete or an A-uncomplete, otherwise the action is performed. In some examples, method 2100 further includes changing the alert status to in-progress if the requested action is to change the alert status to in-progress, as indicated at 2124. In this way, when the alert is an automatically-triggered alert and is currently unresolved, all actions other than reverting the alert to unresolved/uncompleting the alert may be performed, including changing the status to in-progress (manually-triggered alerts may not have the option of setting an in-progress status). Allowed actions for an automatically-triggered, unresolved alert include manual comment, manual escalate, and manual de-escalate, each of which may maintain the status of the alert. Additional allowed actions may include manual in-progress, which may or may not change the status of the alert to complete (depending on the specific configuration of the alert), manual complete, which changes the alert status to manually resolved, automatic complete, which changes the alert status to autoresolved, and manual delete, which deletes the alert (and causes the alert tile for that alert to no longer be displayed). Method 2100 ends.

Returning to 2120, if the alert is not unresolved, method 2100 proceeds to 2126 to determine if the alert has been autoresolved (e.g., determined automatically, by the alert management engine, to be complete based on EMR signals). If the alert has been autoresolved, such as the second alert 404 of FIG. 4 (which was autoresolved based on the alert management engine determining from EMR signals that the abnormal lab value was no longer needing attention), method 2100 proceeds to 2128 to block the requested action if the action is M-complete, M-escalate, M-uncomplete, or A-uncomplete, otherwise the action is performed. For example, the alert may be deleted because the alert has been resolved. Because the alert has been resolved, it cannot be escalated or marked uncomplete. Allowed actions for an automatically-triggered, autoresolved alert include manual comment and manual de-escalate, each of which may maintain the status of the alert. Additional allowed actions may include manual delete and automatic delete, each of which deletes the alert (and causes the alert tile for that alert to no longer be displayed). Method 2100 then ends.

If the alert is determined not to be autoresolved, the alert is instead manually-resolved, and method 2100 proceeds to 2130 to block the requested action if the action is M-complete, M-escalate, or A-complete, otherwise the action is performed. Because the alert has been marked as being complete/resolved, the alert cannot be escalated manually or marked as complete (which may not be presented as an option). However, because the alert was not autoresolved, a manual uncomplete may still be performed to revert the alert status back to incomplete. Allowed actions for an automatically-triggered, manually-resolved alert include manual comment and manual de-escalate, each of which may maintain the status of the alert. Additional allowed actions may include automatic complete, which changes the alert status to autoresolved, and manual and automatic deletes, each of which deletes the alert (and causes the alert tile for that alert to no longer be displayed). Method 2100 then ends.

While method 2100 has been described herein as including blocking certain actions that are specifically requested (either by a user or by the alert management engine), it is to be appreciated that actions described herein as not being allowed/being blocked under certain conditions may not necessarily be presented as an option via the alert management GUI. For example, when an alert is a manually-triggered alert that is currently resolved, the alert tile for that alert may not include an escalation icon and thus a user cannot manually escalate that alert. Thus, in some examples, an action being blocked may also include not presenting that action as an option to be selected.

A technical effect of an integrated alert management system that displays and manages alerts where each alert action and each piece of information about an alert may be viewed/reached though a single alert management GUI is that each alert may be managed more efficiently so that all relevant users may view actions taken on an alert and conflicting actions may be avoided. Another technical effect is that the computing device(s) executing the integrated alert management system may operate more efficiently by reducing redundant storage and reducing or eliminating redundant actions.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   determining an alert for a patient relating to a task for caring for the patient;
   displaying, to a user, the alert via a graphical user interface; and
   responsive to receiving a selection by the user via the graphical user interface, performing one or more actions including one or more of adjusting a status of the alert, snoozing the alert for a specified duration, escalating the alert to one or more users, adding a comment on the alert, and displaying a history of interactions with the alert;
   wherein performing the one or more actions comprises snoozing the alert for the specified duration, the method further comprising automatically prohibiting adjustments to the status of the alert or escalation of the alert while the alert is snoozed for the specified duration.

2. The method of claim 1, further comprising receiving an indication of an update to an electronic medical record (EMR) for the patient, and wherein determining the alert comprises automatically triggering the alert based on the update to the EMR.

3. The method of claim 1, further comprising receiving an indication of an update to an EMR for the patient, and automatically adjusting the status of the alert according to the update to the EMR.

4. The method of claim 1, wherein determining the alert comprises receiving a manual selection, from the user via the graphical user interface, of the alert from a plurality of alerts.

5. The method of claim 1, wherein performing the one or more actions comprises adjusting the status of the alert to indicate a completion level of the task according to the selection via the graphical user interface, wherein the selection comprises a toggling of a status icon in the graphical user interface.

6. The method of claim 1, further comprising displaying, in the graphical user interface adjacent to the alert, a plurality of icons corresponding to the one or more actions, displaying, adjacent to the alert in the graphical user interface, an expanded menu associated with an icon of the plurality of icons responsive to the user toggling the icon, and wherein receiving the selection by the user via the graphical user interface comprises receiving input to the menu from the user.

7. A method, comprising:
  determining an alert for a patient relating to a task for caring for the patient;
  displaying, to a user, the alert via a graphical user interface; and responsive to receiving a selection by the user via the graphical user interface, performing one or more actions including one or more of adjusting a status of the alert, snoozing the alert for a specified duration, escalating the alert to one or more users, adding a comment on the alert, and displaying a history of interactions with the alert;
  wherein determining the alert comprises receiving a manual selection, from the user via the graphical user interface, of the alert from a plurality of alerts;
  the method further comprising manually triggering the alert responsive to receiving the manual selection, and prohibiting an automatic adjustment to the status of the alert according to an update to an EMR while the alert is manually triggered.

8. A system, comprising:
  memory storing instructions; and
  a processor configured to execute the instructions to:
    receive an indication that an alert for a patient relating to a task for caring for the patient has been triggered; and
    in response to the alert being triggered, display, on a graphical user interface, an alert tile that includes an alert identifier, a first icon indicating an alert status of the alert, a second icon indicating a snooze status of the alert, a third icon indicating a comment status of the alert, and a fourth icon indicating an escalation status of the alert, the alert tile further including a link to a history of the alert and a delete icon;
    wherein the first icon is selectable to adjust the alert status of the alert, the second icon is selectable to cause display of a snooze sub-menu configured to receive input to set a snooze timer for the alert, the third icon is selectable to cause display of a comment sub-menu configured to receive input to set a comment for the alert, the fourth icon is selectable to cause display of an escalation sub-menu configured to receive input to escalate the alert, the link to the history of the alert is selectable to cause display of the history of the alert, and the delete icon is selectable to cause the alert to be deleted and the alert tile removed from the graphical user interface.

9. The system of claim 8, wherein the first icon being selectable to adjust the alert status includes the first icon being selectable to adjust the alert status from incomplete to in-progress with a first input, adjust the alert status from in-progress to complete with a second input, and adjust the alert status from complete to incomplete with a third input.

10. The system of claim 8, wherein receiving the indication that the alert has been triggered includes receiving an indication that a user has manually triggered the alert, and wherein the first icon being selectable to adjust the alert status includes the first icon being selectable to adjust the alert status from incomplete to complete with a first input and adjust the alert status from complete to incomplete with a second input.

11. The system of claim 8, wherein the instructions are further executable to analyze signals from an EMR database and trigger the alert in response to the signals.

12. A system, comprising:
  memory storing instructions; and
  a processor configured to execute the instructions to:
    receive an indication that an alert for a patient relating to a task for caring for the patient has been triggered; and
    in response to the alert being triggered, display, on a graphical user interface, an alert tile that includes an alert identifier, a first icon indicating an alert status of the alert, a second icon indicating a snooze status of the alert, a third icon indicating a comment status of the alert, and a fourth icon indicating an escalation status of the alert, the alert tile further including a link to a history of the alert and a delete icon;
    wherein the instructions are further executable to analyze signals from an EMR database and trigger the alert in response to the signals; and
    wherein the instructions are further executable to, after the alert is triggered, continue to analyze the signals from the EMR database and adjust the alert status to autocomplete, and in response to the alert status being adjusted to autocomplete, adjust a visual appearance of the first icon.

13. The system of claim 12, wherein the instructions are further executable, once the alert status is adjusted to autocomplete, block a user from escalating the alert.

14. A method, comprising:
  receiving an indication that an alert for a patient relating to a task for caring for the patient has been triggered;
  in response to the alert being triggered, displaying, on a graphical user interface, an alert tile identifying the alert;
  responsive to receiving a request that an action be performed regarding the alert, applying a set of rules to determine if the requested action is permissible based on an alert status of the alert and the requested action; and
  if the requested action is permissible, performing the requested action, otherwise, blocking the requested action;
  wherein the requested action includes adjusting the alert status of the alert, snoozing the alert for a specified duration, escalating the alert to one or more users, adding a comment on the alert, displaying a history of interactions with the alert, or deleting the alert; and
  wherein the alert is an automatically-triggered alert, wherein the alert status of the alert is manually-resolved, and wherein applying the set of rules includes applying the set of rules to determine, based on the requested action being escalating the alert to one or more users, that the requested action is not permissible and blocking the requested escalation.

15. A method, comprising:

receiving an indication that an alert for a patient relating to a task for caring for the patient has been triggered;

in response to the alert being triggered, displaying, on a graphical user interface, an alert tile identifying the alert;

responsive to receiving a request that an action be performed regarding the alert, applying a set of rules to determine if the requested action is permissible based on an alert status of the alert and the requested action; and if the requested action is permissible, performing the requested action, otherwise, blocking the requested action;

wherein the requested action includes adjusting the alert status of the alert, snoozing the alert for a specified duration, escalating the alert to one or more users, adding a comment on the alert, displaying a history of interactions with the alert, or deleting the alert; and wherein the alert is an automatically-triggered alert, wherein the alert status of the alert is manually-resolved, and wherein applying the set of rules includes applying the set of rules to determine, based on the requested action being automatically changing the alert status to automatically-resolved, that the requested action is permissible and performing the requested change of the alert status.

16. A method, comprising:

receiving an indication that an alert for a patient relating to a task for caring for the patient has been triggered;

in response to the alert being triggered, displaying, on a graphical user interface, an alert tile identifying the alert;

responsive to receiving a request that an action be performed regarding the alert, applying a set of rules to determine if the requested action is permissible based on an alert status of the alert and the requested action; and if the requested action is permissible, performing the requested action, otherwise, blocking the requested action;

wherein the requested action includes adjusting the alert status of the alert, snoozing the alert for a specified duration, escalating the alert to one or more users, adding a comment on the alert, displaying a history of interactions with the alert, or deleting the alert; and wherein the alert is a manually-triggered alert, wherein the alert status of the alert is resolved, and wherein applying the set of rules includes applying the set of rules to determine, based on the requested action being a manually-requested escalation of the alert, that the requested action is not permissible and blocking the requested escalation.

* * * * *